(12) United States Patent
Lampropoulos et al.

(10) Patent No.: US 10,638,964 B2
(45) Date of Patent: May 5, 2020

(54) BIOPSY DEVICE AND METHOD OF USE

(71) Applicant: Merit Medical Systems, Inc., South Jordan, UT (US)

(72) Inventors: Fred Lampropoulos, Salt Lake City, UT (US); Ayad Agha, Paradise Valley, AZ (US); Nicholas Gerald Accisano, Howell, NJ (US)

(73) Assignee: Merit Medical Systems, Inc., South Jordan, UT (US)

( * ) Notice: Subject to any disclaimer, the term of this patent is extended or adjusted under 35 U.S.C. 154(b) by 180 days.

(21) Appl. No.: 14/134,280

(22) Filed: Dec. 19, 2013

(65) Prior Publication Data

US 2014/0171826 A1    Jun. 19, 2014

Related U.S. Application Data

(60) Provisional application No. 61/739,112, filed on Dec. 19, 2012.

(51) Int. Cl.
*A61B 5/15* (2006.01)
*A61B 10/02* (2006.01)
(Continued)

(52) U.S. Cl.
CPC .... *A61B 5/150992* (2013.01); *A61B 10/0266* (2013.01); *A61B 10/0275* (2013.01);
(Continued)

(58) Field of Classification Search
CPC .............. A61B 10/04; A61B 5/150992; A61B 2017/00331; A61B 10/0275
See application file for complete search history.

(56) References Cited

U.S. PATENT DOCUMENTS 4,785,826 A     11/1988  Ward
4,946,445 A  *   8/1990  Lynn ..................... A61M 39/04
                                                    604/192
(Continued)

FOREIGN PATENT DOCUMENTS

AT          366546       6/1976
EP          0966920      12/1999
(Continued)

OTHER PUBLICATIONS

U.S. Appl. No. 29/495,581, filed Jul. 2, 2014, Snow.
(Continued)

*Primary Examiner* — Daniel L Cerioni
*Assistant Examiner* — Yasmeen S Warsi
(74) *Attorney, Agent, or Firm* — Stoel Rives LLP

(57) ABSTRACT

Various components of an interventional therapy assembly are disclosed. One such component is a pointer which may be configured to indicate the disposition of another portion or component of the assembly. A rotary indexing device which may be configured to control or facilitate rotation of other components is also disclosed. Further, various components of an elongate instrument having flexible segments and operative segments are also disclosed. In some embodiments, the elongate instrument may comprise a biopsy assembly and may be used in connection with other components of the disclosed assembly.

18 Claims, 27 Drawing Sheets

(51) Int. Cl.
*A61B 10/04* (2006.01)
*A61B 17/221* (2006.01)
*A61B 17/29* (2006.01)
*A61B 90/11* (2016.01)
*A61F 2/95* (2013.01)
*A61B 17/00* (2006.01)
*A61B 17/32* (2006.01)

(52) U.S. Cl.
CPC ............ *A61B 10/04* (2013.01); *A61B 17/221* (2013.01); *A61B 17/29* (2013.01); *A61B 90/11* (2016.02); *A61B 2017/00331* (2013.01); *A61B 2017/00455* (2013.01); *A61B 2017/320032* (2013.01); *A61F 2/95* (2013.01); *F04C 2270/0421* (2013.01)

(56) References Cited

U.S. PATENT DOCUMENTS

| | | | |
|---|---|---|---|
| 5,172,702 | A | 12/1992 | Leigh et al. |
| 5,601,572 | A * | 2/1997 | Middleman ............ A61B 10/02 606/139 |
| 5,655,542 | A | 8/1997 | Weilandt |
| 5,788,651 | A | 8/1998 | Weilandt |
| 5,800,389 | A | 9/1998 | Burney et al. |
| 5,842,999 | A | 12/1998 | Pruitt et al. |
| D418,223 | S | 12/1999 | Phipps et al. |
| D428,150 | S | 7/2000 | Ruf et al. |
| 6,126,617 | A | 10/2000 | Weilandt et al. |
| 6,146,338 | A * | 11/2000 | Gardeski ............ A61M 25/0147 600/585 |
| 6,196,978 | B1 | 3/2001 | Weilandt et al. |
| 6,322,523 | B2 | 11/2001 | Weilandt et al. |
| 6,340,356 | B1 * | 1/2002 | Navia ................ A61B 17/12022 604/104 |
| D457,955 | S | 5/2002 | Bilitz |
| 6,419,641 | B1 * | 7/2002 | Mark ................ A61B 10/0275 600/564 |
| D463,555 | S | 9/2002 | Etter et al. |
| 6,488,662 | B2 | 12/2002 | Sirimanne |
| 6,497,687 | B1 | 12/2002 | Blanco |
| 6,656,195 | B2 | 12/2003 | Peters et al. |
| D490,152 | S | 5/2004 | Myall et al. |
| 7,041,065 | B2 | 5/2006 | Weilandt et al. |
| 7,247,160 | B2 | 7/2007 | Seiler et al. |
| D571,009 | S | 6/2008 | Smith et al. |
| 7,470,237 | B2 | 12/2008 | Beckman et al. |
| D586,916 | S | 2/2009 | Faulkner et al. |
| D598,543 | S | 8/2009 | Vogel et al. |
| 7,608,048 | B2 | 10/2009 | Goldenberg |
| D612,044 | S | 3/2010 | Scheibe |
| D612,051 | S | 3/2010 | Ruf |
| D619,251 | S | 7/2010 | Justiniano-Garcia et al. |
| D628,293 | S | 11/2010 | Ruf |
| 8,043,362 | B2 | 10/2011 | Gorman et al. |
| 8,137,317 | B2 | 3/2012 | Osypka |
| 9,392,998 | B2 | 7/2016 | Snow |
| 2001/0009979 | A1 | 7/2001 | Weilandt et al. |
| 2004/0133124 | A1 * | 7/2004 | Bates ................ A61B 10/0275 600/564 |
| 2004/0215103 | A1 | 10/2004 | Mueller et al. |
| 2005/0054947 | A1 | 3/2005 | Goldenberg |
| 2005/0125017 | A1 | 6/2005 | Kudma et al. |
| 2006/0085019 | A1 | 4/2006 | Cote et al. |
| 2006/0195175 | A1 * | 8/2006 | Bregulla .................. A61F 2/91 623/1.15 |
| 2007/0027407 | A1 | 2/2007 | Miller |
| 2007/0078472 | A1 | 4/2007 | Singh |
| 2007/0142744 | A1 | 6/2007 | Provencher |
| 2007/0179403 | A1 | 8/2007 | Heske et al. |
| 2007/0250037 | A1 | 10/2007 | Brimhall et al. |
| 2008/0051820 | A1 | 2/2008 | Gong et al. |
| 2008/0200833 | A1 | 8/2008 | Hardin et al. |
| 2008/0228104 | A1 | 9/2008 | Uber et al. |
| 2008/0281223 | A1 | 11/2008 | Goldenberg |
| 2008/0300507 | A1 | 12/2008 | Figueredo et al. |
| 2009/0275966 | A1 | 1/2009 | Mitusina |
| 2009/0118704 | A1 * | 5/2009 | Sharrow ................ A61L 29/02 604/523 |
| 2009/0143698 | A1 | 6/2009 | Janssens |
| 2009/0259200 | A1 | 10/2009 | Lampropoulos et al. |
| 2009/0299220 | A1 | 12/2009 | Field et al. |
| 2010/0010526 | A1 | 1/2010 | Mitusina |
| 2010/0130887 | A1 | 5/2010 | Selis |
| 2010/0168773 | A1 | 7/2010 | Funderburk et al. |
| 2011/0251631 | A1 | 10/2011 | Trees et al. |
| 2012/0220894 | A1 | 8/2012 | Melsheimer |
| 2012/0226101 | A1 | 9/2012 | Tinkham et al. |
| 2013/0131548 | A1 | 5/2013 | McGhit et al. |
| 2013/0150795 | A1 | 6/2013 | Snow |
| 2014/0100479 | A1 | 4/2014 | Tripp et al. |
| 2014/0207021 | A1 | 7/2014 | Snow |
| 2015/0201963 | A1 | 1/2015 | Snow |
| 2015/0045828 | A1 | 2/2015 | Mcarthur et al. |
| 2015/0094751 | A1 | 4/2015 | Chen et al. |
| 2015/0201917 | A1 | 6/2015 | Snow |
| 2016/0089208 | A1 | 3/2016 | Vetter |

FOREIGN PATENT DOCUMENTS

| | | |
|---|---|---|
| JP | 2005511989 | 4/2005 |
| JP | 2008510596 | 4/2008 |
| JP | 2008104856 | 5/2008 |
| JP | 2009279096 | 12/2009 |
| WO | WO1996/22733 | 8/1996 |
| WO | WO1999/44505 | 9/1999 |
| WO | WO2006/013389 | 2/2006 |
| WO | 2012167216 A2 | 12/2012 |

OTHER PUBLICATIONS

U.S. Appl. No. 14/598,457, filed Jun. 16, 2015, Snow.
U.S. Appl. No. 14/600,660, filed Jan. 20, 2015, Snow.
Shuttle® and CT-Core® Semi-Automatic devices; Updated to the website between Nov. 8, 2012-Jan. 24, 2013. Accessed website on Jun. 27, 2014 at http://www.vigeohealthcare.com/gb/int_radiplogy.html.
International Search Report and Written Opinion dated May 1, 2014 for PCT/US2014/012043.
International Search Report and Written Opinion dated Apr. 3, 2014 for PCT/US2013/076418.
International Search Report and Written Opinion dated Apr. 30, 2015 for PCT/US2015/012002.
International Search Report and Written Opinion dated Jan. 16, 2015 for PCT/US2015/011746.
Extended European Search Report dated Aug. 26, 2016 for EP13863978.6.
International Search Report and Written Opinion dated Jun. 23, 2015 for PCT/US2013/076418.
International Preliminary Report dated Jul. 19, 2016 for PCT/US2015/011746.
Office Action dated Mar. 20, 2017 for U.S. Appl. No. 14/598,457.
Office Action dated Aug. 28, 2017 for U.S. Appl. No. 14/598,457.
Office Action dated Feb. 26, 2019 for U.S. Appl. No. 15/184,551.
Office Action dated Mar. 1, 2019 for U.S. Appl. No. 14/598,457.
Office Action dated Sep. 4, 2018 for U.S. Appl. No. 14/598,457.
Office Action dated Oct. 9, 2018 for U.S. Appl. No. 15/184,551.
Office Action dated Aug. 9, 2019 for U.S. Appl. No. 14/598,457.
Office Action dated Jan. 25, 2018 for U.S. Appl. No. 14/598,457.
Office Action dated Mar. 26, 2018 for U.S. Appl. No. 15/184,551.

* cited by examiner

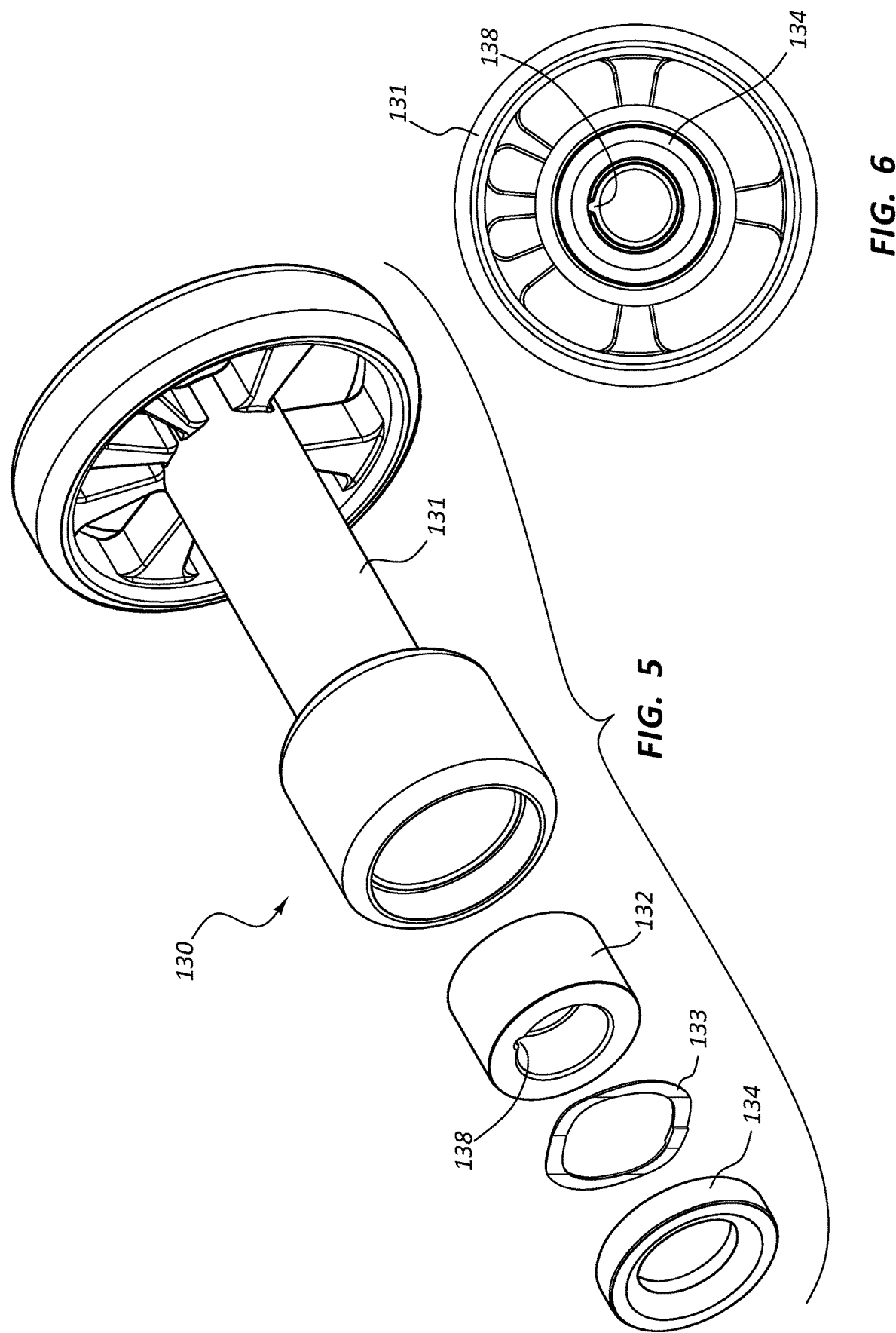

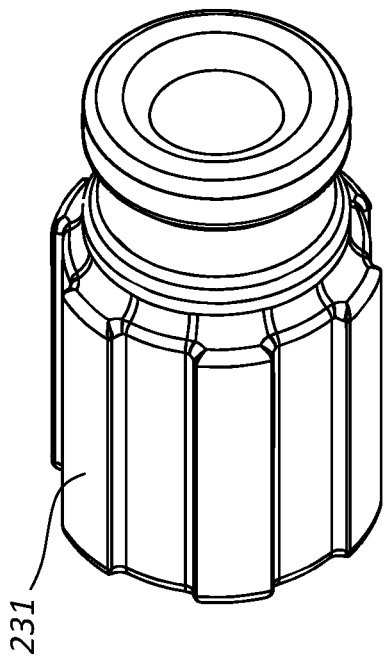
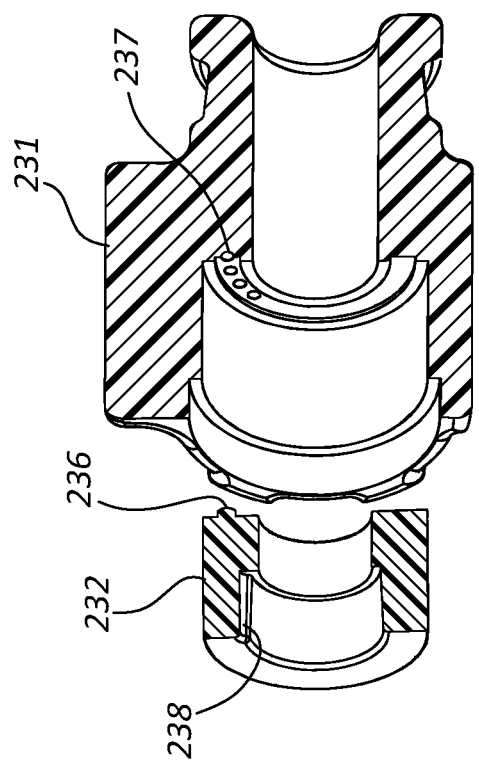
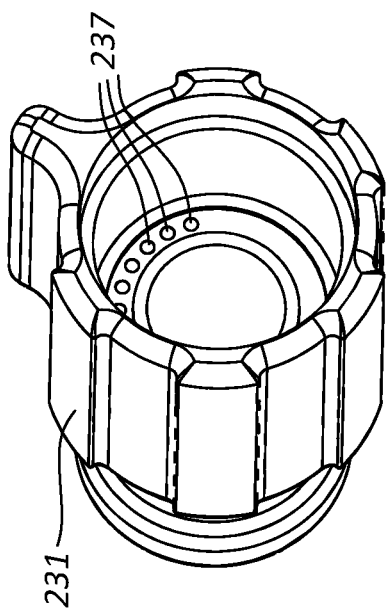
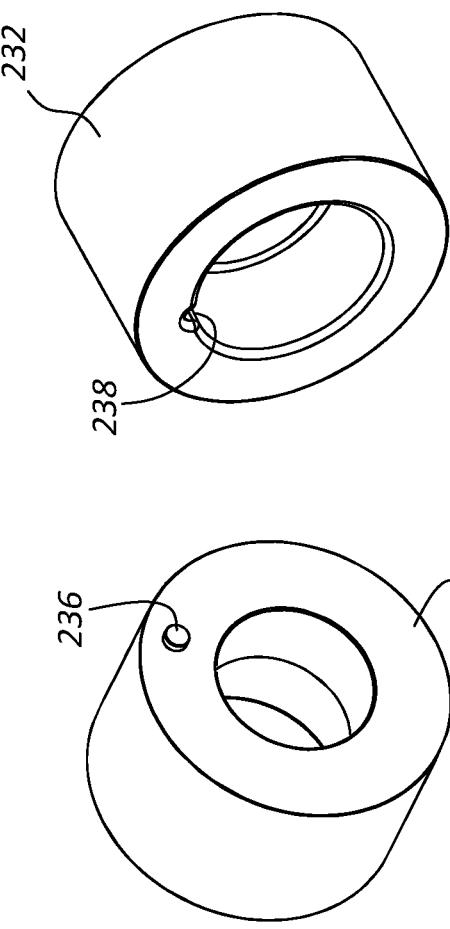
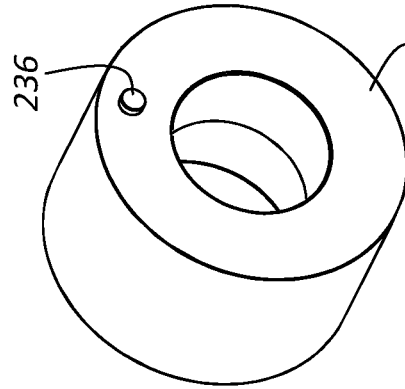

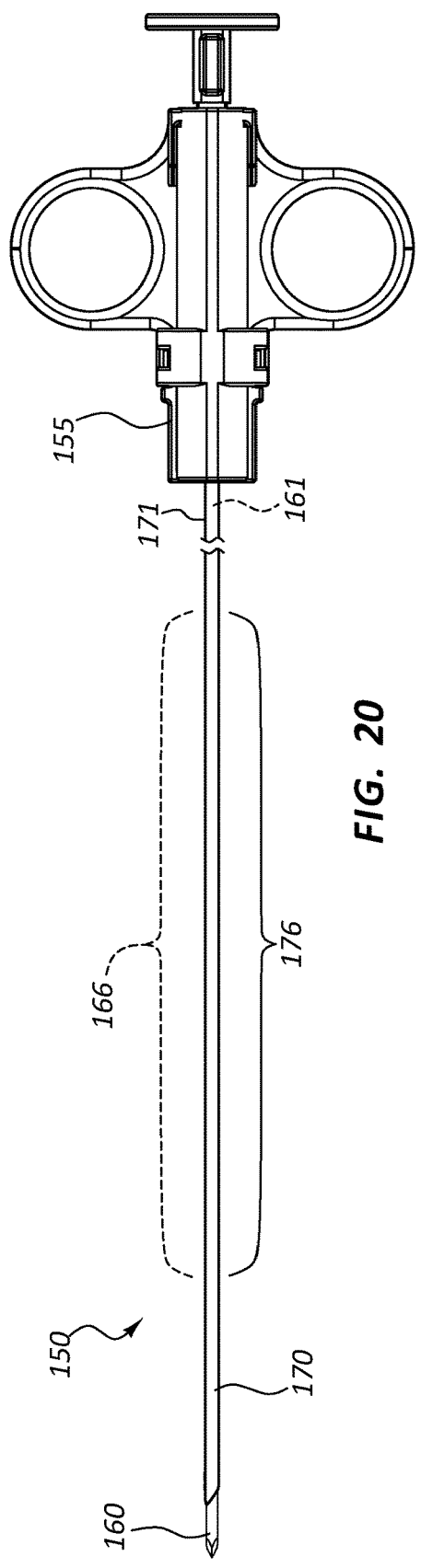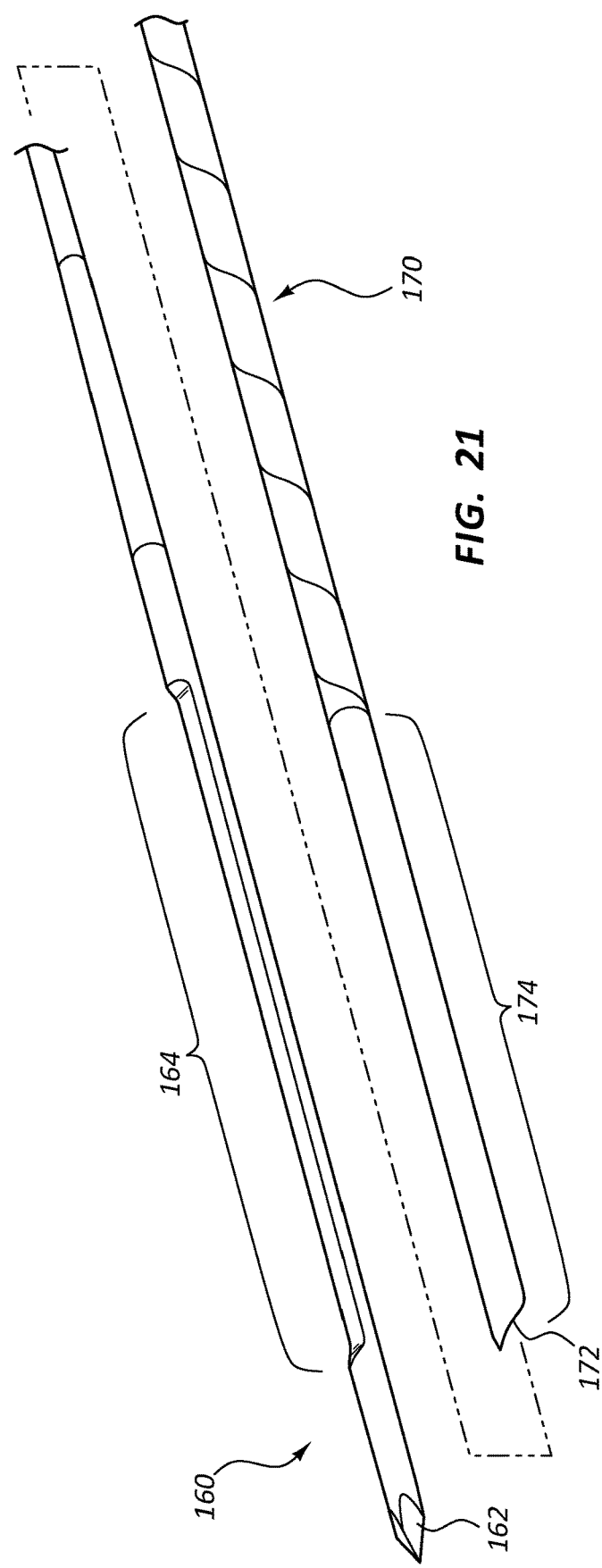

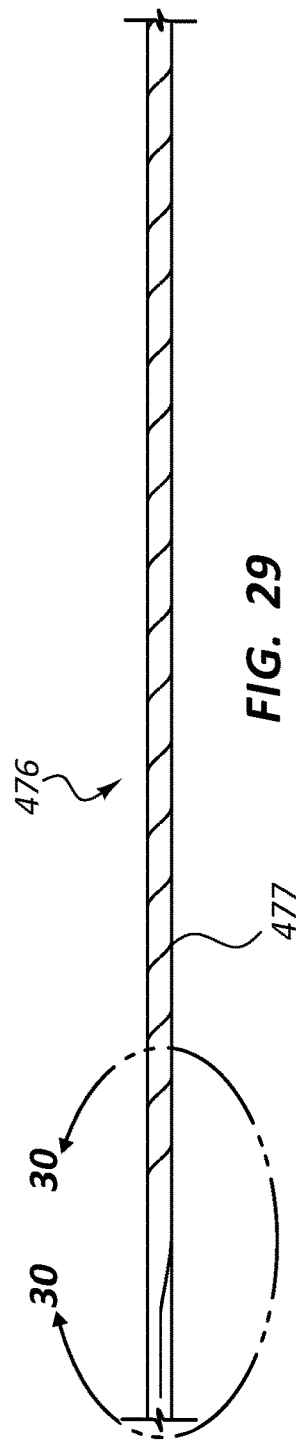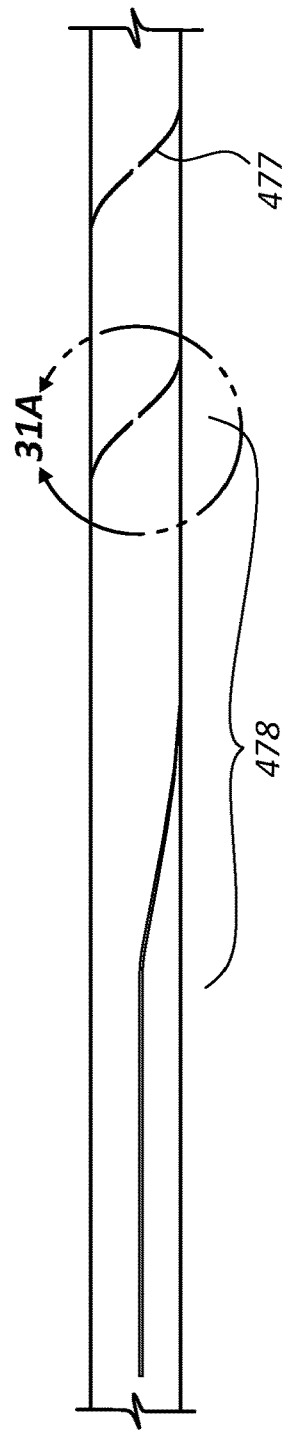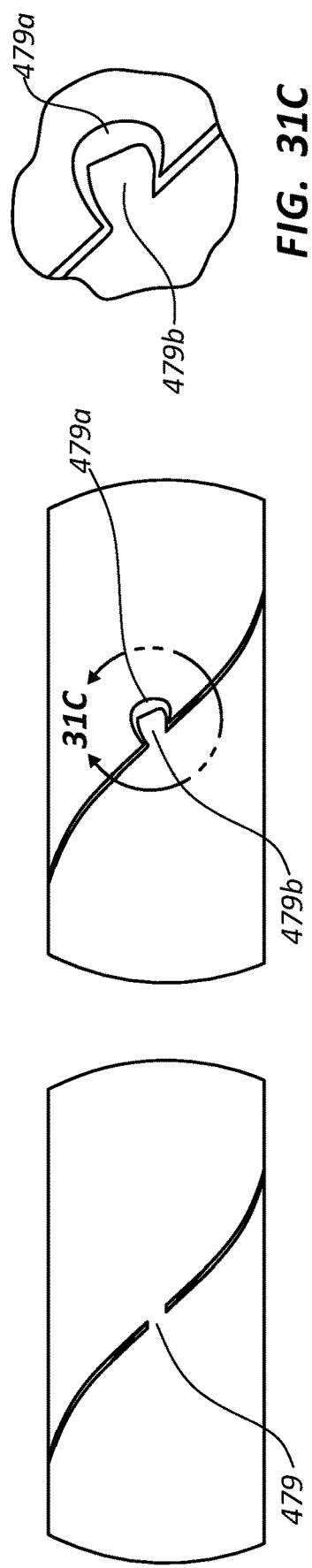

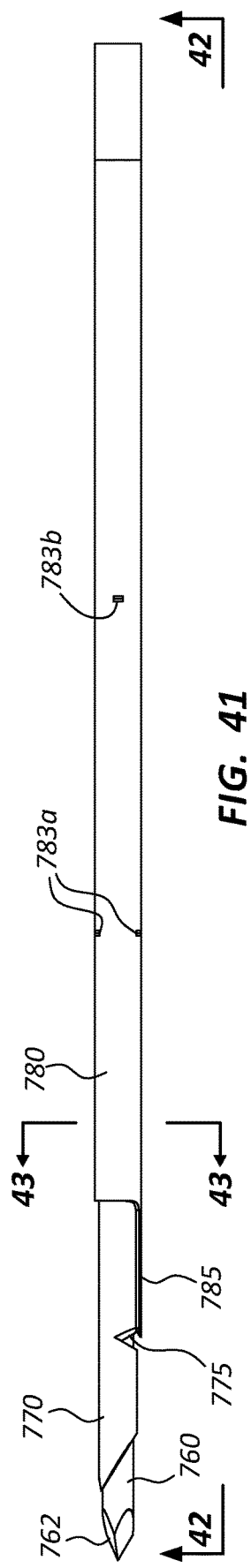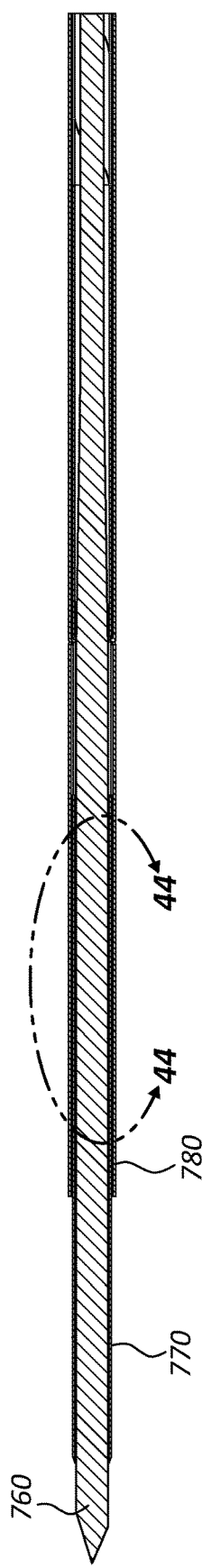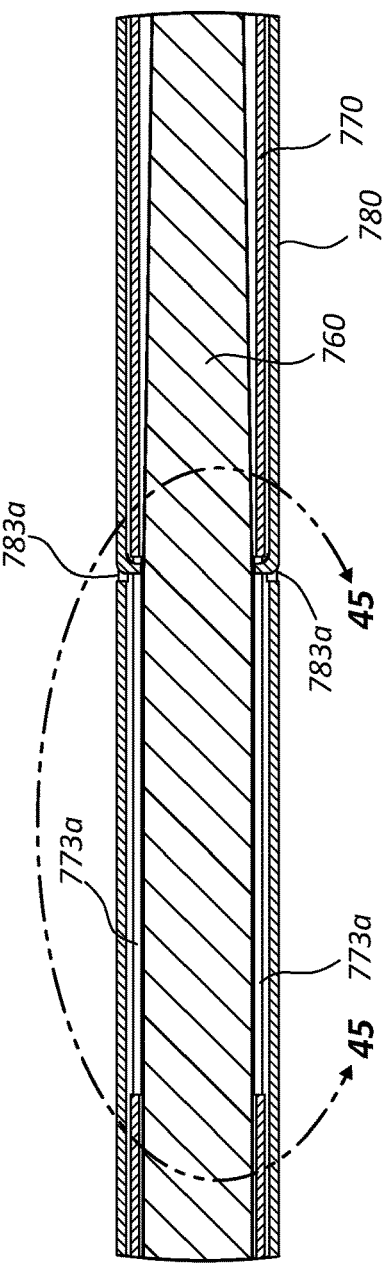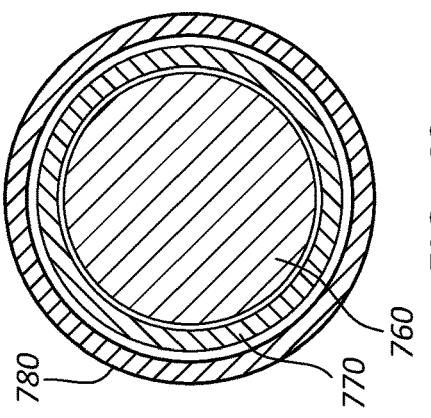
FIG. 41
FIG. 42
FIG. 43
FIG. 44

BIOPSY DEVICE AND METHOD OF USE

RELATED APPLICATIONS

This application claims priority to U.S. Provisional Application No. 61/739,112 filed on Dec. 19, 2012 and titled "Biopsy Device and Method of Use," which is hereby incorporated by reference in its entirety.

TECHNICAL FIELD

The present disclosure relates generally to medical devices. More specifically, the present disclosure relates to transvascular devices or other minimally invasive devices. In some embodiments the present disclosure relates to transvascular liver therapy devices, including transjugular liver biopsy devices.

BRIEF DESCRIPTION OF THE DRAWINGS

The embodiments disclosed herein will become more fully apparent from the following description and appended claims, taken in conjunction with the accompanying drawings. The drawings depict only typical embodiments, which embodiments will be described with additional specificity and detail in connection with the drawings in which:

FIG. 5 is an exploded view of the rotary indexer of the assembly of FIG. 1.

FIG. 6 is a front assembled view of the rotary indexer of FIG. 5.

FIG. 8 is a first perspective view of the base of the rotary indexer of FIG. 7.

FIG. 9 is a second perspective view of the base of the rotary indexer of FIG. 7.

FIG. 10 is a first perspective view of the rotary member of the rotary indexer of FIG. 7.

FIG. 11 is a second perspective view of the rotary member of the rotary indexer of FIG. 7.

FIG. 12 is a cross-sectional view of the rotary member and base of the rotary indexer of FIG. 7.

FIG. 20 is a side view of the biopsy assembly of the assembly of FIG. 1.

FIG. 21 is an exploded perspective view of the stylet and cannula of the biopsy assembly of FIG. 20.

FIG. 29 is a side view of another embodiment of a flexible segment of a component of a biopsy assembly.

FIG. 30 is an enlarged view of a portion of the flexible segment of FIG. 29, taken around line 30-30.

FIG. 31A is an enlarged view of a portion of the flexible segment of FIG. 30, taken around line 31A.

FIG. 31B is an enlarged view of another embodiment of a portion of a flexible segment, analogous to the view of FIG. 31A.

FIG. 31C is an enlarged view of a portion of FIG. 31B.

FIG. 41 is a side view of a portion of the biopsy assembly of FIG. 36.

FIG. 42 is a cross-sectional view of the portion of the biopsy assembly of FIG. 41, taken through plane 42-42.

FIG. 43 is a cross-sectional view of the portion of the biopsy assembly of FIG. 41, taken through plane 43-43.

FIG. 44 is an enlarged view of a portion of the cross-sectional view of FIG. 42, taken around line 44-44.

DETAILED DESCRIPTION

Various therapies and procedures may be performed through transvascular or other minimally invasive techniques. For example, one or more instruments may be introduced into the vasculature of a patient and advanced to a treatment site, and a therapy may then be performed.

In some embodiments, vascular access techniques may be used to treat the liver. For example, a device may be configured for use in a transjugular liver biopsy procedure; i.e., a procedure directed to retrieving a liver sample through a device introduced at the jugular vein of a patient.

It will be readily understood that the components of the embodiments as generally described and illustrated in the Figures herein could be arranged and designed in a wide variety of different configurations. Thus, the following more detailed description of various embodiments, as represented in the Figures, is not intended to limit the scope of the disclosure, but is merely representative of various embodiments. While the various aspects of the embodiments are presented in drawings, the drawings are not necessarily drawn to scale unless specifically indicated.

The phrases "connected to" and "coupled to" refer to any form of interaction between two or more entities, including mechanical, electrical, magnetic, electromagnetic, fluid, and thermal interaction. Two components may be coupled to each other even though they are not in direct contact with each other. For example, two components may be coupled to each other through an intermediate component.

The directional terms "proximal" and "distal" are used herein to refer to opposite locations on a medical device. The proximal end of the device is defined as the end of the device closest to the practitioner when the device is in use by the practitioner. The distal end is the end opposite the proximal end, along the longitudinal direction of the device, or the end furthest from the practitioner.

Figure 1:
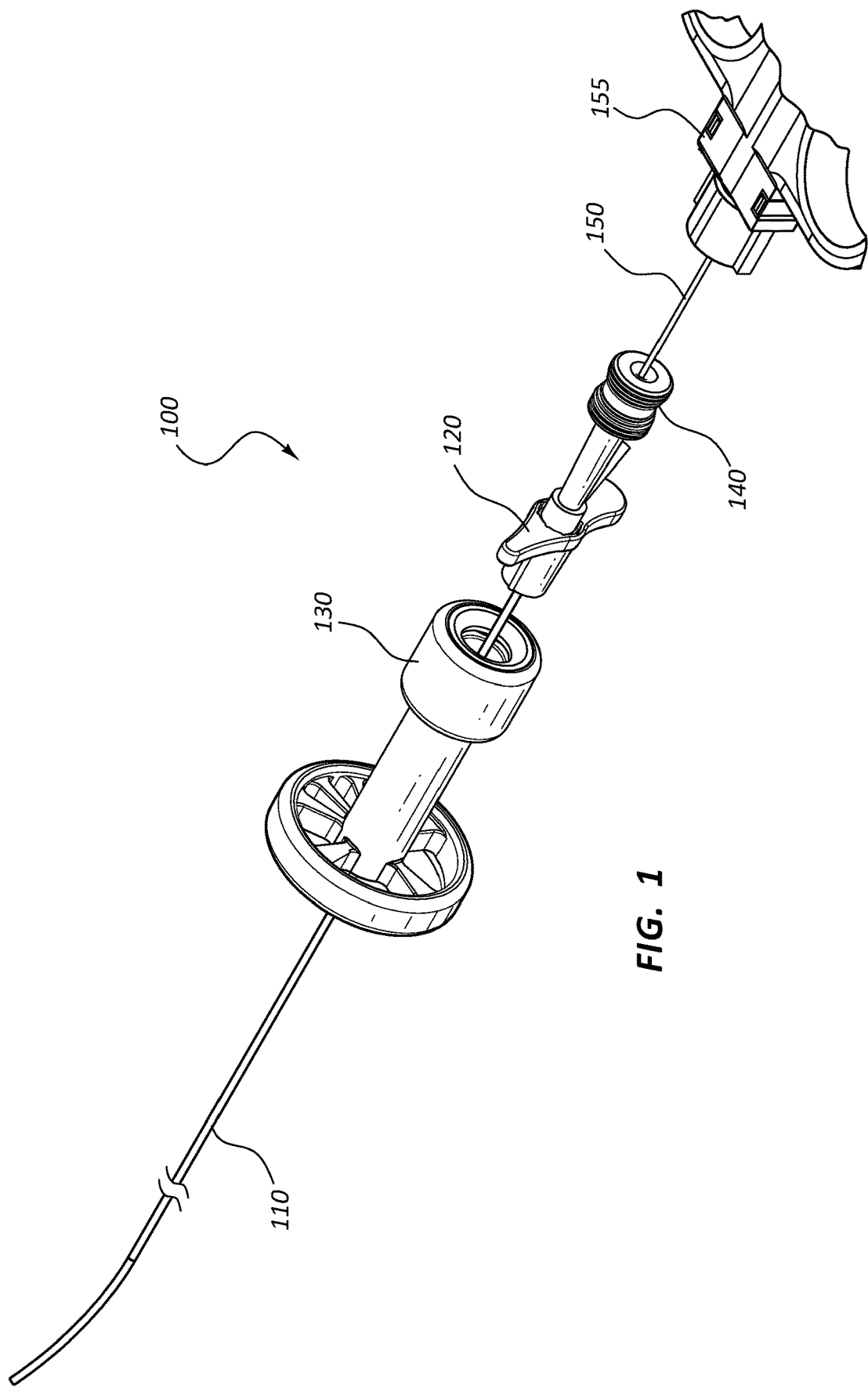
FIG. 1 is a perspective view of a transvascular biopsy assembly in a first configuration.

FIG. 1 is a perspective view of a transvascular biopsy assembly 100 in a first configuration. The assembly 100 of FIG. 1 comprises various components as further detailed below. In other embodiments, any combination of the individual components may comprise an assembly or subassembly for use in connection with a transvascular procedure.

In the embodiment of FIG. 1, the assembly 100 comprises an introducer sheath 110 coupled to a pointer 120 adjacent the proximal end of the introducer sheath 110. A delivery lumen (105 of FIG. 3) may extend from a proximal end of the valve 140, through the pointer 120, to a distal end of the introducer sheath 110. A biopsy device 150 may be configured to be disposed within the delivery lumen (105 of FIG. 3). The assembly may further comprise a rotary indexer 130. These components are disclosed in further detail below. A handle 155 of the biopsy device 150 is also shown in FIG. 1.

A biopsy device 150 may be configured to be disposed within the delivery lumen (105 of FIG. 3) of the introducer sheath 110, pointer 120, and valve 140. In the configuration of FIG. 1, the biopsy device 150 is shown partially disposed within the delivery lumen (105 of FIG. 3). In some embodiments the biopsy device 150 may be configured to be delivered through the vasculature of a patient to obtain a tissue sample from the patient. For example, the biopsy device 150 may be configured to obtain a liver sample by introducing the biopsy device 150 into a vessel of the liver, then obtaining a sample. In other embodiments the biopsy device may be configured to obtain a tissue sample from another part of the body. The biopsy device 150 may be configured to obtain a partial core tissue sample, a full core tissue sample, a blood or other fluid sample from a particular region of the body, and so forth. Other treatment devices or assemblies (used in connection with or in place of the biopsy device 150) are within the scope of this disclosure. For example, the assembly 100 may be configured to guide or deliver devices such as stent deployment tools, snares, balloons, probes, forceps, and so forth. In some embodiments, the assembly 100 may be configured for use in connection with a transjugular intrahepatic portosystemic shunt ("TIPS") procedure. In some such embodiments, the assembly 100 may or may not comprise a biopsy device 150.

Figure 2:
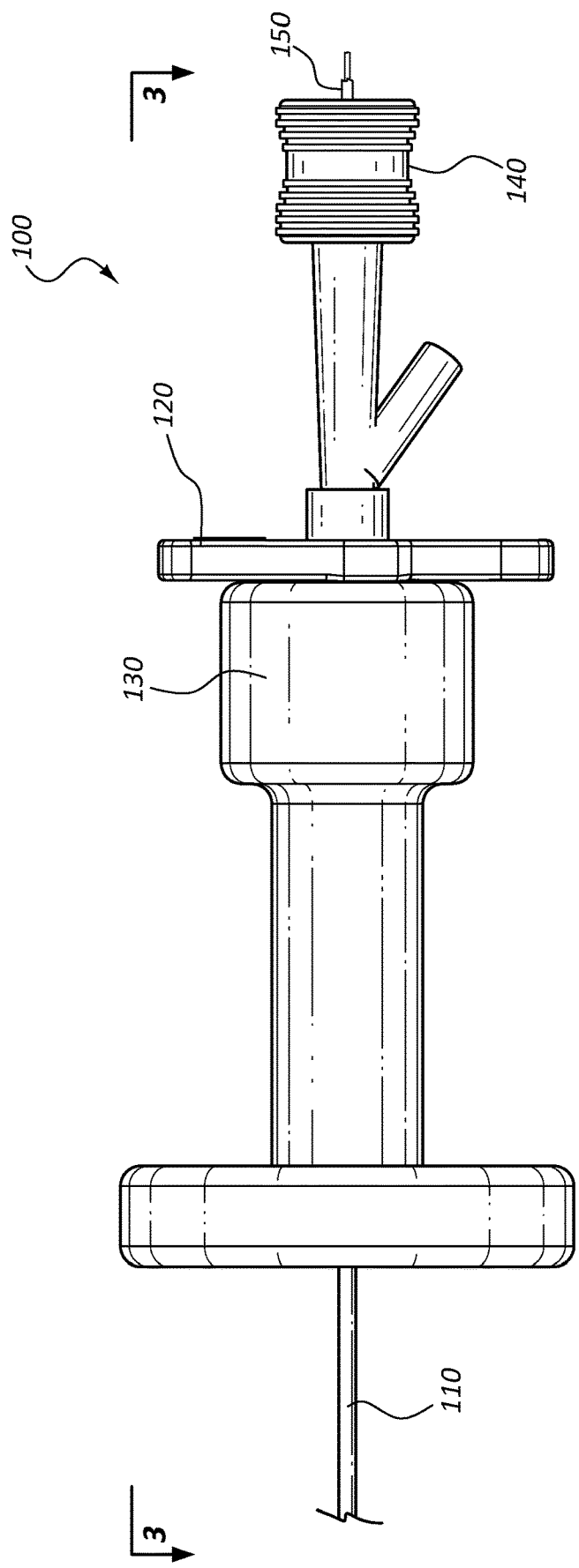
FIG. 2 is a front elevation view of a portion the transvascular biopsy assembly of FIG. 1 in a second configuration.
Figure 3:
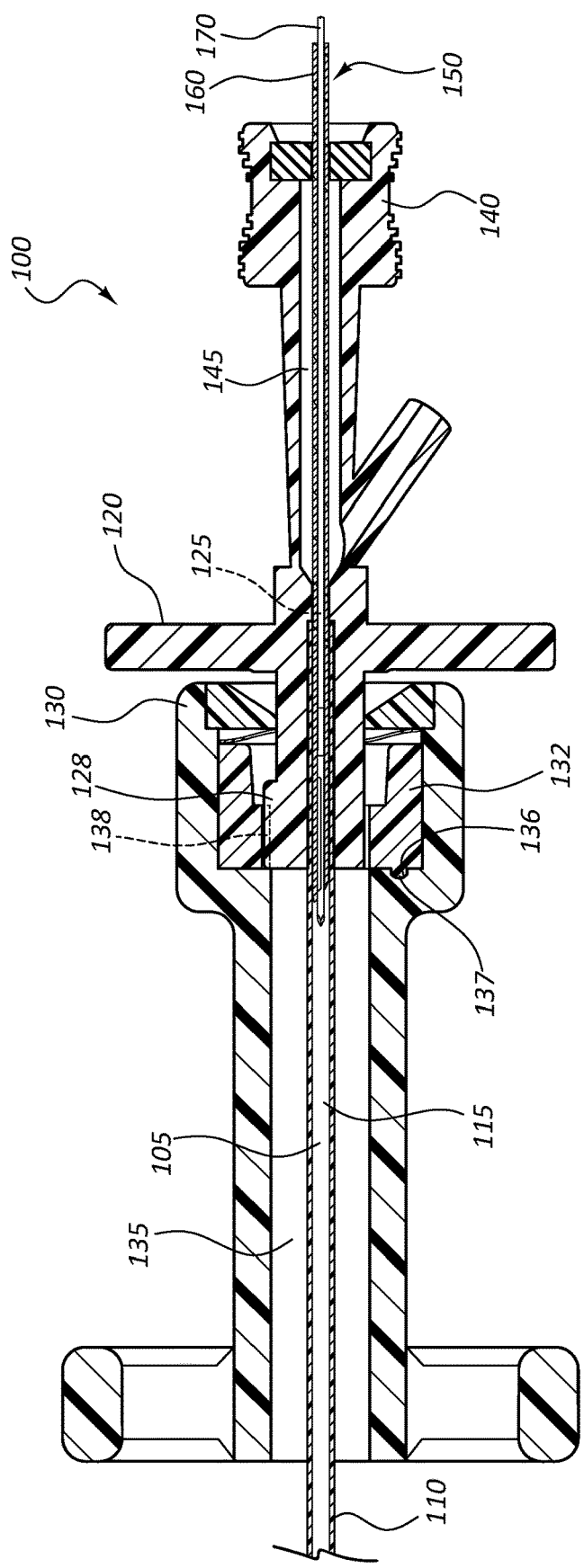
FIG. 3 is a cross-sectional view of the portion of the transvascular biopsy assembly of FIG. 2 taken through plane 3-3.

FIG. 2 is a front elevation view of a portion of the transvascular biopsy assembly 100 of FIG. 1 in a second configuration, and FIG. 3 is a cross-sectional view of the portion of the transvascular biopsy assembly 100 of FIG. 2. Referring to FIGS. 1-3, the biopsy device 150 may be axially displaceable within the delivery lumen 105 of the assembly 100. In the configuration of FIGS. 2 and 3, the biopsy device 150 is shown partially advanced within the delivery lumen 105, such that a distal end of the biopsy device 150 is disposed within a portion of the delivery lumen 105 adjacent the rotary indexer 130. The introducer sheath 110, the pointer 120, and the valve 140 may each comprise a lumen: an introducer sheath lumen 115, a pointer lumen 125, and a valve lumen 145. The introducer sheath lumen 115, the pointer lumen 125, and the valve lumen 145 may be aligned such that these lumen collectively comprise the delivery lumen 105 of the assembly 100. In other embodiments or configurations, the assembly 100 may or may not include each of the introducer sheath 110, the pointer 120, and the valve 140. In such embodiments, the delivery lumen 105 may only comprise a subset of the introducer sheath lumen 115, the pointer lumen 125, and the valve lumen 145. For example, in some configurations the assembly 100 may not include a pointer 120. In such instances the valve lumen 145 may be disposed directly adjacent the introducer sheath lumen 115 to form the delivery lumen 105 of the assembly 100. In other embodiments, additional components of the assembly may be disposed such that lumens or openings in these additional components also comprise the delivery lumen 105. As shown in FIG. 3, the rotary indexer 130 may also comprise a rotary indexer lumen 135. In the illustrated embodiment, the delivery lumen 105 runs through the rotary indexer lumen 135, though the rotary indexer lumen 135 may not comprise a direct portion of the delivery lumen 105. In other embodiments, these components may be arranged such that a portion of the rotary indexer lumen 135 comprises a portion of the delivery lumen 105.

Further, in the configuration of FIGS. 2 and 3, the pointer 120 has been axially advanced with respect to the rotary indexer 130 (as compared to the configuration of FIG. 1) such that a ridge 128 of the pointer 120 is engaged with a slot 138 of the rotary indexer 130. This engagement may couple a rotary member 132 of the rotary indexer 130 to the pointer 120 such that rotation of the pointer 120 also rotates the rotary member 132.

Figure 4:
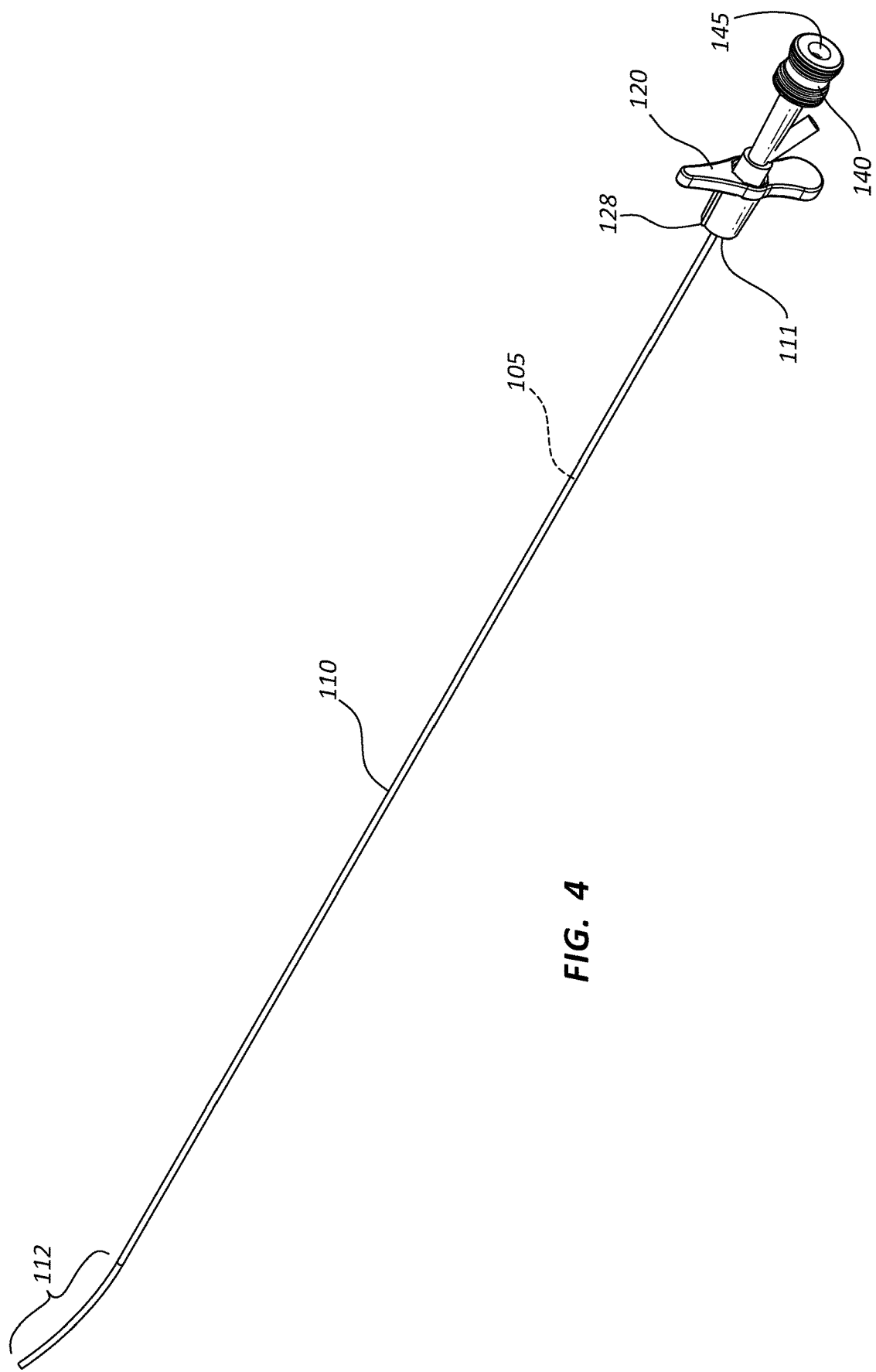
FIG. 4 is a perspective view of the introducer sheath, pointer, and valve of the assembly of FIG. 1.

FIG. 4 illustrates the introducer sheath 110, pointer 120, and valve 140 of the assembly 100 of FIG. 1. In some embodiments, the pointer 120 may be fixedly coupled adjacent a proximal end 111 of the introducer sheath 110, including embodiments wherein these components are integrally formed. In other embodiments, the pointer 120 may be removably coupled to the introducer sheath 110. The pointer 120 may be coupled to the introducer sheath 110 such that the pointer 120 and introducer sheath 110 are constrained to rotate together about a longitudinal axis of the components. The introducer sheath 110 may be formed of a single material, comprise a laminate material, and/or comprise a reinforced material. In some embodiments the introducer sheath 110 may be configured with a particular stiffness to facilitate a particular procedure. For example, the introducer sheath 110 may be sufficiently stiff to facilitate advancement of the introducer sheath 110 along the vasculature of a patient.

The introducer sheath 110 may comprise a curved distal tip 112. The magnitude of the curve may be greater or smaller than shown in the illustrated embodiment. The curved distal tip 112 may be configured to facilitate steering of the introducer sheath 110 as the introducer sheath 110 is advanced within a body lumen of a patient. The curved distal tip 112 may also or alternatively be configured to access a particular portion of the patient's body during a therapy. For example, during a transjugular liver biopsy procedure, an introducer sheath 110 may be advanced from an insertion point at a patient's jugular vein, through the vasculature to the patient's liver. The curved distal tip 112 of the introducer sheath 110 may be configured to direct instruments passed through the introducer sheath 110 (e.g., a biopsy device) such that the instruments emerge from the sheath and contact the desired tissue. Rotation of the introducer sheath 110 about its longitudinal axis may be configured to alter or direct the orientation or disposition of the curved distal tip 112 of the introducer sheath 110.

The pointer 120 may be disposed such that its orientation corresponds to the orientation or direction of the curved distal tip 112 of the introducer sheath 110. For example, the curved distal tip 112 of the introducer sheath may be curved substantially within a plane, and a transverse axis of the pointer 120 may lie substantially within the same plane. Thus, rotation of the introducer sheath 110 (which may be coupled to the pointer 120) may cause the pointer 120 to rotate such that the pointer 120 extends in the same direction as the curved distal tip 112 of the introducer sheath 110. When the introducer sheath 110 is in use, the curved distal tip 112 may be disposed within a patient, and thus not directly observable by a practitioner. The pointer 120, however, may be disposed outside the patient and thereby provide the practitioner with a visual indication of the orientation of the curved distal tip within the patient's body.

An introducer sheath 110 or any other elongate instrument configured to be positioned or otherwise controlled by rotating a curved portion thereof (such as the curved distal tip 112 of introducer sheath 110) may be utilized in a variety of procedures within a patient's body, including transvascular procedures. In some instances, a practitioner may control or observe the rotational position of a curved distal tip 112 through use of a pointer 120 and/or a rotary indexer 130. These components, and their relationship to rotation of another device, are further discussed below.

A pointer analogous to pointer 120 of FIG. 4 may be used in connection with any elongate instrument. For example an analogous pointer may be coupled to a drainage catheter, a stent delivery device, a guidewire, or any other device configured to be inserted into a patient's body. Some such devices may be configured for use within the vasculature of a patient, while others may be configured for insertion into other body lumens, or configured for insertion into portions of the body not comprising lumens.

The pointer 120 of FIG. 4 further comprises a ridge 128 disposed on a distal portion of the pointer 120. The ridge 128 may be configured to engage another element of an assembly to couple the rotational displacement of the pointer 120 with the rotational displacement of the coupled element. For example, as discussed in connection with FIG. 3, the ridge 128 may couple the pointer 120 to a rotary member (132 of FIG. 3) of a rotary indexer (130 of FIG. 3). In some embodiments the ridge 128 or other engagement member may be disposed on the introducer sheath 110 or some other component of the assembly. The rotary indexer (130 of FIG. 3) is discussed in more detail below.

As shown in FIG. 4, a valve 140 may be coupled to a proximal end of the pointer 120. The valve 140 may be configured to control flow and access to the valve lumen 145 and/or the delivery lumen 105 of the assembly. In some embodiments the valve 140 may be directly coupled to the pointer 120, including embodiments wherein the valve 140 and pointer 120 are integrally formed. In other embodiments, the valve 140 may be coupled directly to the introducer sheath 110 and may be integrally formed with the introducer sheath 110. In some embodiments, the valve 140 may be provided in connection with an introducer sheath 110 but no pointer 120. Similarly, an introducer sheath 110 and pointer 120 may be configured for use without a valve 140.

FIG. 5 is an exploded view of the rotary indexer 130 of the assembly 100 of FIG. 1. FIG. 6 is a front assembled view of the rotary indexer 130. The rotary indexer 130 may be configured to control the rotation and/or indicate the rotational position of certain components of the assembly. The rotary indexer 130 may comprise a base 131 configured to receive a rotary member 132. The rotary member 132 may be configured to be rotatable relative to the base 131 when the rotary indexer 130 is assembled. The rotary member 132 may be configured with an engagement feature, such as slot 138, configured to engage other components. Thus, rotation of the rotary member 132 with respect to the base 131 may also rotate an engaged component relative to the base 131.

For example, referring collectively to FIGS. 1-6, an assembly 100 may be configured such that the pointer 120 comprises a ridge 128 configured to engage the slot 138 of the rotary member 132. In the illustrated embodiment, rotation of the introducer sheath 110 and pointer 120 may thus be coupled to rotation of the rotary member 132 with respect to the base 131. In the illustrated embodiment, the ridge 128 of the pointer 120 is configured to slide into the slot 138 of the rotary member 130 when the components are engaged. In other embodiments, the pointer 120 or some other component, such as the introducer sheath 110, may be fixedly coupled to the rotary member 132. In still further embodiments, the rotary indexer 130 may be configured such that a component such as a medical device is coupled to the base 131 such that rotation of the base 131 with respect to the rotary member 132 (which may be coupled to the pointer 120) rotates the medical device with respect to the pointer 120. In such an arrangement, the relative position of the pointer 120 with respect to the base 131 may still be configured to indicate the rotational position of the medical device.

In some embodiments, the base 131 may comprise visual indicia corresponding to the position of the pointer 120 with respect to the base 131 which indicate the position of the pointer 120 (and therefore the curved distal tip 112 of the introducer sheath 110). For example, numbers, colors, lines, and so forth on the base 131 may align with the pointer 120 and indicate the relative rotation of the curved distal tip 112 of the introducer sheath 110.

The rotary member 132 may also be configured with detents or other catch mechanisms configured to releasably couple the rotary member 132 to the base 131 such that the rotary member 132 cannot easily rotate when the detents or catch mechanisms are engaged. Interaction between the rotary member 132 and the base 131 may thus allow a practitioner to rotatably displace the rotary member 132 (and therefore the pointer 120 and introducer sheath 110 in some embodiments) a certain amount, then release the rotated components. Interaction with the base 131 may be configured to resist unwanted rotational displacement of these components, for example, when the practitioner desires to leave the components in place for a portion of a therapeutic procedure.

In the embodiment of FIGS. 5 and 6, the rotary member 132 may be coupled to the base 131 by interaction with a biasing element 133 and a retainer 134. The retainer 134 may be coupled to the base 131 and the biasing element 133 configured to bias the rotary member 132 into contact with a portion of the base 131.

Figure 7:
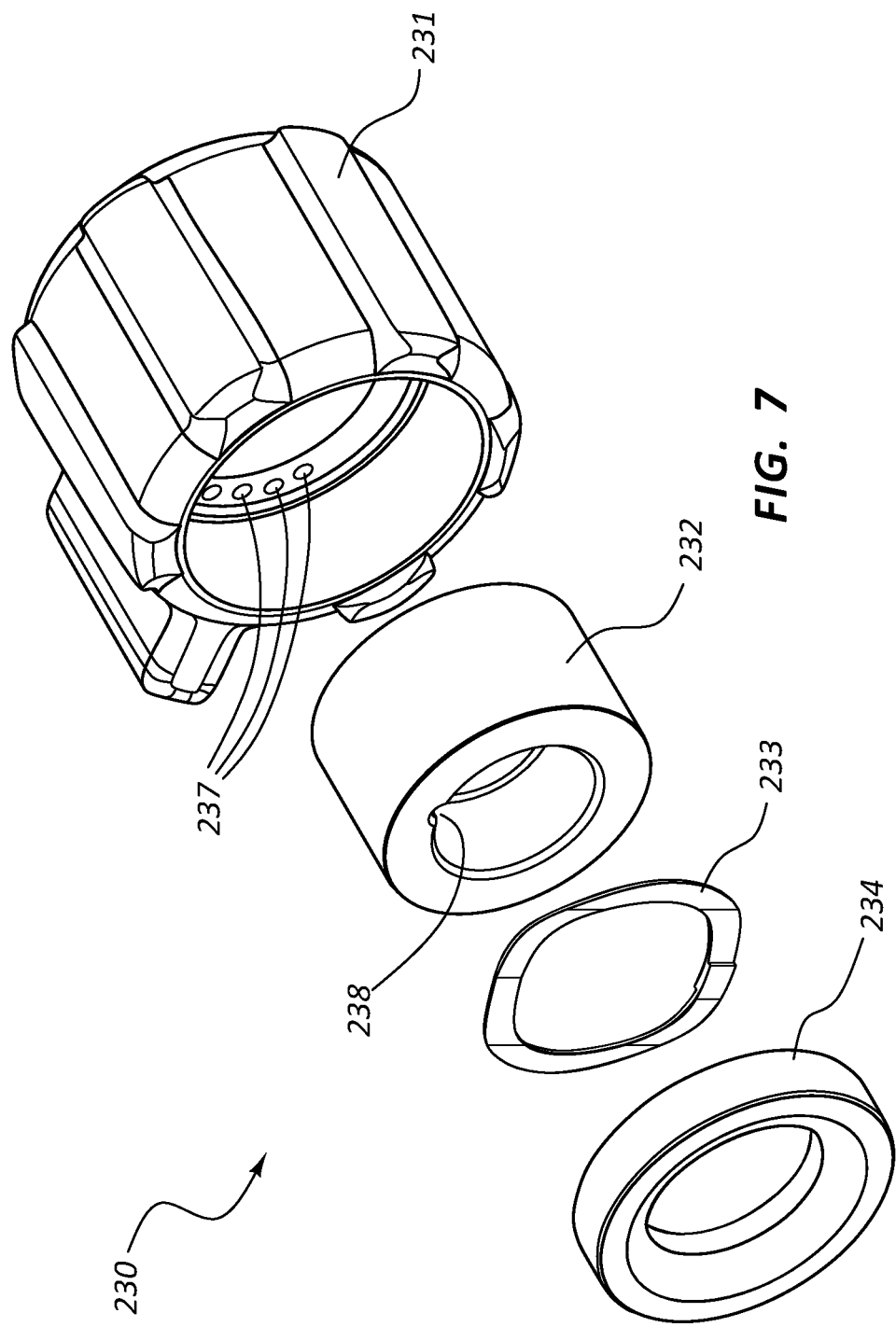
FIG. 7 is an exploded view of another embodiment of a rotary indexer.

FIG. 7 is an exploded view of another embodiment of a rotary indexer 230. The embodiment of FIG. 7 may include components that resemble components of the embodiment of FIG. 5 in some respects. For example, the embodiment of FIG. 7 includes a rotary member 232 that may resemble the rotary member 132 of the embodiment of FIG. 5. It will be appreciated that all the illustrated embodiments have analogous features and components. Accordingly, like or analogous features are designated with like reference numerals, with the leading digits incremented to "2." Relevant disclosure set forth above regarding similarly identified features thus may not be repeated hereafter. Moreover, specific features of the system and related components shown in FIG. 7 may not be shown or identified by a reference numeral in the drawings or specifically discussed in the written description that follows. However, such features may clearly be the same, or substantially the same, as features depicted in other embodiments and/or described with respect to such embodiments. Accordingly, the relevant descriptions of such features apply equally to the features of the system and related components of FIG. 7. Any suitable combination of the features, and variations of the same, described with respect to the system and components illustrated in FIG. 5 can be employed with the system and components of FIG. 7, and vice versa. This pattern of disclosure applies equally to further embodiments depicted in subsequent figures and described hereafter. Moreover, this pattern of disclosure and numbering applies to any of the components or systems herein disclosed, not simply to various embodiments of rotary indexers. Thus, any component or assembly depicted in any embodiment herein may have analogous features to, or function in an analogous manner to, components or assemblies of other embodiments.

The rotary indexer 230 shown in FIG. 7 comprises a base 231, a rotary member 232, a biasing element 233, and a retainer 234. Recessed portions 237 are also shown in a surface of the base 231. When the rotary indexer 230 is assembled, the retainer 234 and biasing element 233 may interact with the rotary member 232 to bias the rotary member 232 into contact with the surface of the base 231 in which the recessed portions 237 are formed. FIGS. 8-9 are perspective views of the base 231 of the rotary indexer 230, FIGS. 10-11 are perspective views of the rotary member 232 of the rotary indexer 230, and FIG. 12 is a cross-sectional view of the rotary member 232 and base 231.

Referring to FIGS. 7-12, the rotary indexer 230 may be configured such that detents between the rotary member 232 and the base 231 releasably couple the rotary member 232 to the base 231 such that the rotary member 232 may only rotate with respect to the base 231 when the detents are not engaged. In the illustrated embodiment, the base 231 may include one or more recessed portions 237 in a surface of the base 231. The rotary member 232 may include a protrusion 236 configured to interact with the recessed portions 237. The protrusion 236 and recessed portions 237 may function as detents, tending to constrain rotation of the rotary member 232 with respect to the base 231 when the protrusion 236 is disposed within a recessed portion 237. The biasing element 233 may tend to bias the rotary member 232 such that disengaging the protrusion 236 from a recessed portion 237 may be accomplished by overcoming the force exerted by the biasing element 233 on the rotary member 232 such that the rotary member 232 may move distally with respect to the base 231, allowing the protrusion 236 to disengage and the rotary member 232 to rotate with respect to the base 231.

The recessed portions 237 may be disposed in an arcuate path, creating multiple detents in the path of rotational displacement of the rotary member 232. The detents may be spaced in a variety of configurations; for example the detents could be equally spaced about an arc, could be disposed closer or farther apart along particular segments of the arc, could increase or decrease in spacing in one direction or the other, and so forth. In some embodiments, the detents may be spaced such that they represent a particular displacement of the rotary member 232 and thus, in some embodiments, the curved distal tip (112 of FIG. 4) of an introducer sheath or other component coupled to the rotary member 232. In some embodiments the adjacent detents may represent rotational displacement of about 5 to about 25 degrees, of about 10 to about 20 degrees, or of about 15 degrees. In some embodiments there may be from about five to about nine detents disposed in an arc, or more or fewer detents disposed in an arc or complete circle.

The spacing of the detents may be configured for use in connection with a particular therapy. For example, a particular procedure may be configured to obtain multiple tissue samples from differing locations in the body. In one instance, a practitioner may dispose a biopsy device (150 of FIG. 1) within a vessel of a patient's liver via transvascular access. The practitioner may then obtain a first tissue sample, rotate the rotary member 232 to the next detent, obtain another tissue sample, and so forth.

The interaction of the rotary member 232 and the base 231 may be configured to provide visual indicia of the rotational position of an instrument coupled to the rotary member 232. For example, as discussed above, a pointer (120 of FIG. 1) may be coupled to the rotary member 232 and correspond to marks or other indicia on the base 231. Interaction of the rotary member 232 and base 231 may also be configured to provide audible or tactile indicia of the relative displacement of an instrument. For example, the rotary indexer 230 may be configured such that the device creates an audible or tactile response as the detents between the rotary member 232 and base 231 engage and disengage.

As an analogous component, the rotary indexer 130 of FIGS. 1-3 and 5-6 may be configured with detents in an analogous manner to those described in connection with the rotary indexer 230 of FIGS. 7-12. Referring again to FIG. 1, the rotary indexer 130 may comprise a base 131, a rotary member 132, a biasing element 133, and a retainer 134 disposed in an analogous manner to that discussed in connection with the embodiment of FIG. 7. Any configuration of detents or catches between the rotary member 132 and the base 131 are within the scope of this disclosure. In some embodiments the detents may be similar to those described in connection with FIGS. 7-12. For example, the cross-sectional view of FIG. 3 illustrates a protrusion 136 and a recessed portion 137. As with the other embodiments, additional recessed portions may be positioned in a rotational path about the base 131.

Other arrangements of detents are within the scope of this disclosure. For example recesses may be formed in an outside diameter of one component with arms or tabs of a second component configured to interact therewith. Further, one component may comprise a plurality of protrusions configured to interact with a plurality of recesses. The components and detents may be arranged to allow full 360-degree rotation of the parts.

Any of the embodiments of rotary indexers or related components described herein may be used in connection with any other component or assembly described herein. Referring again to FIG. 1, a rotary indexer 130 may comprise a portion of a medical device assembly, such as transvascular biopsy assembly 100. At various points during a therapy, a practitioner may rotate a portion of the assembly, utilizing the rotary indexer 130 to control the degrees of rotation (e.g., the number of stops the indexer 130 is rotated) or track the amount of rotation (e.g., by observing visual indicia, including the disposition of a pointer 120 with respect to the rotary indexer 130).

One exemplary procedure which may utilize a rotary indexer 130 is a transjugular liver biopsy. A practitioner may advance a liver biopsy device to a desired location within a lumen of the liver. The practitioner may then obtain a first sample, rotate the rotary indexer 130 between one or more stops, and obtain another sample. The rotary indexer 130 may facilitate controlling the spacing of where samples are obtained. A rotary indexer 130 may similarly be used in connection with a drainage catheter or other instrument disposed within a patient's body. For example, a practitioner may wish to rotate a drainage catheter in order to access various locations within the body. A rotary indexer 130 may facilitate control of the spacing of such displacement.

A rotary indexer 130 may also be used in connection with a TIPS procedure. A practitioner may dispose a cannula within a first lumen of the liver, then attempt to advance the cannula through the liver to a second lumen of the liver, the cannula connecting the two lumens. In order to ascertain whether the cannula has accessed the second lumen, the practitioner may attempt to draw blood back through the cannula; if the tip of the cannula is disposed in the second lumen, blood or other fluids from that lumen should draw through the cannula. In instances where sufficient fluid is not drawn back, the practitioner may determine the cannula is disposed within liver tissue, not within a lumen. The practitioner may then rotate the cannula in order to access a different spot, and attempt to locate the second lumen. A rotary indexer 130 may be configured to indicate rotational positions a practitioner has already tested as well as control rotation of the cannula.

It is within the scope of this disclosure to utilize a rotary indexer 130 with various other procedures or treatments. For example, placement of catheters, balloons, snares, stents, and so forth may each be done during a procedure wherein one or more components are rotated. Rotary indexers 130 may be configured to facilitate or control such rotation in any such procedure.

FIGS. 13-19 are various embodiments of valves which may be configured for use in connection with a transvascular access assembly such as the transvascular biopsy assembly 100 of FIG. 1. The assembly 100 of FIG. 1 comprises a valve 140 coupled adjacent a proximal end of the pointer 120. Any of the valves described herein may be used in place of and/or in an analogous manner to the valve 140 of FIG. 1. As with the assembly 100 of FIG. 1, these valves may be coupled to the assembly at various points, including embodiments wherein a valve is directly coupled to the introducer sheath 110. Luer connectors, threads, or other releasable coupling mechanisms may be used to couple the valves and/or other components.

In the embodiment of FIG. 1, a pointer 120 is coupled adjacent an end of the valve 140. The pointer 120 may be configured to be rotatable with respect to the valve 140, or the pointer may be fixedly coupled to the valve 140. In any of the embodiments discussed below, the valves may be releasably or fixedly coupled to a pointer (such as 120 of FIG. 1) and/or an introducer sheath (such as 110 of FIG. 1) when used in an assembly.

Valves, such as hemostasis valves, may be configured to allow vascular access while still maintaining a degree of hemostasis at the insertion site. For example, the assembly 100 of FIG. 1 may be configured such that the introducer sheath 110 is disposed within the vasculature. The valve 140 may be configured to allow a practitioner to access the delivery lumen (105 of FIG. 3) with an elongate device (such as biopsy device 150 of FIG. 1) while selectively closing the valve 140 to prevent blood flow through the delivery lumen (105 of FIG. 3).

Analogous to the valve 140 of FIG. 1, the valves (and related components) described below have analogous reference numerals with the leading digit incremented between embodiments.

Figure 13:
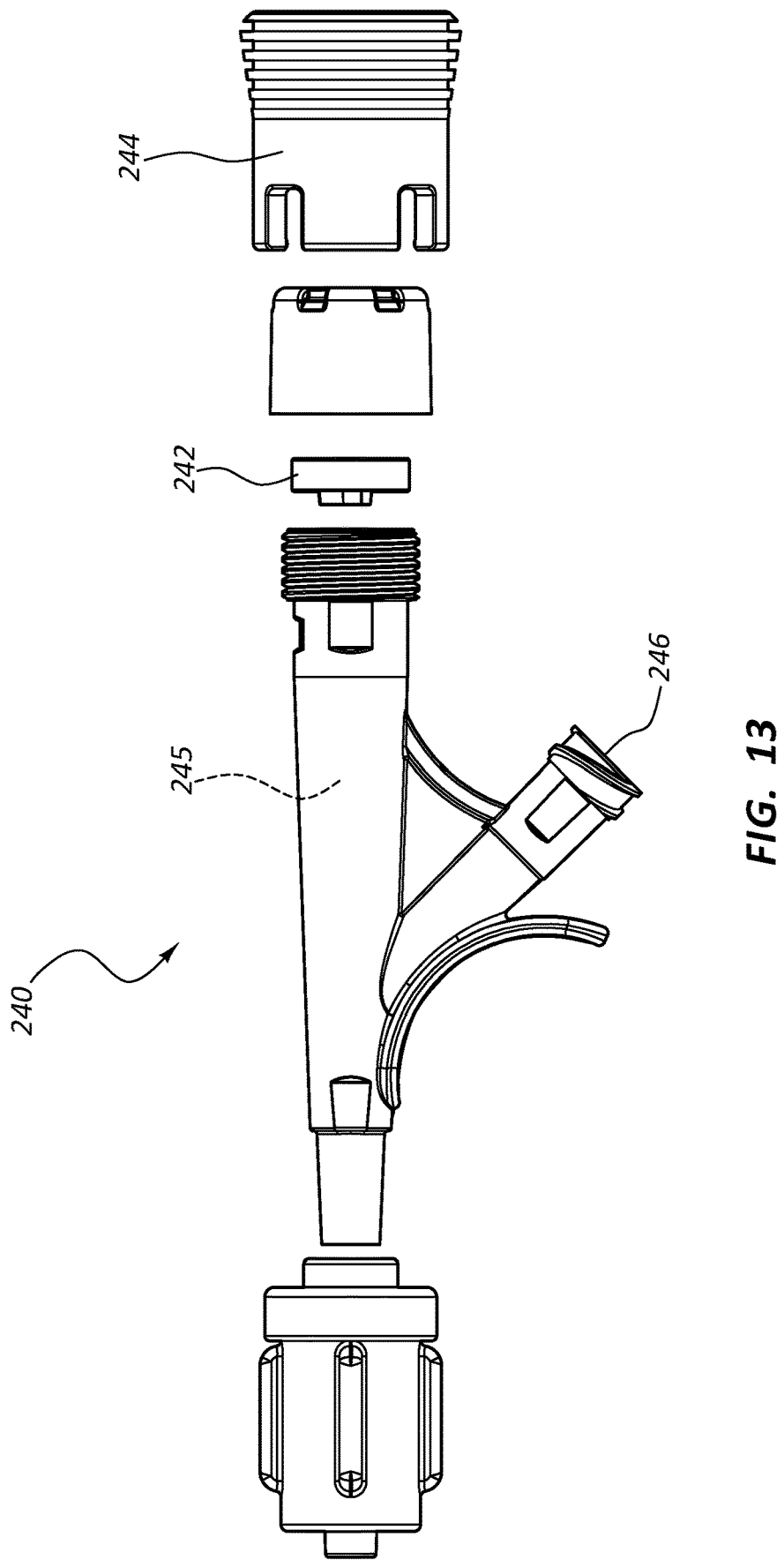
FIG. 13 is an exploded view of an embodiment of a valve.

FIG. 13 is an exploded view of an embodiment of a valve 240. The valve 240 may comprise a seal 242, an actuating component 244, and a valve lumen 245. The valve 240 may be configured such that the practitioner may selectively open and close the seal 242 to selectively allow access to the valve lumen 245. For example, a practitioner may open the seal 242 in order to introduce an instrument into the valve lumen 245 and close the seal 242 in order to prevent bleed back when the therapy allows. In some instances the seal 242 may be configured to seal the valve lumen 245 when no instrument is disposed therein and/or to seal about an instrument that has been introduced into the valve lumen 245.

The valve 240 may be configured with an actuator 244 configured to selectively open and close the seal 242. In some embodiments, displacement of the actuator 244 may be configured to open and/or close the seal 242. The actuator 244 may be configured to toggle between open and closed seal 242 positions, meaning the practitioner may displace the actuator 244 to change the configuration of the seal 242 and release the actuator 244 without the seal 242 changing configurations. In other embodiments the seal 242 or actuator 244 may be biased in either the closed or open position, requiring the practitioner to maintain pressure or contact with the actuator 244 to maintain the non-biased position. In the embodiment of FIG. 13, axially displacing the actuator 244 with respect to the seal 242 may be configured to open and/or close the seal 242.

The valve 240 may further comprise a side port 246. The side port 246 may be configured to allow a practitioner to introduce fluid flow (e.g., contrast fluid, saline, etc.) into the valve lumen 245 whether the seal 242 is open or closed. Flow through or pressure within the side port 246 may prevent bleed back through the side port 246.

Figure 14:
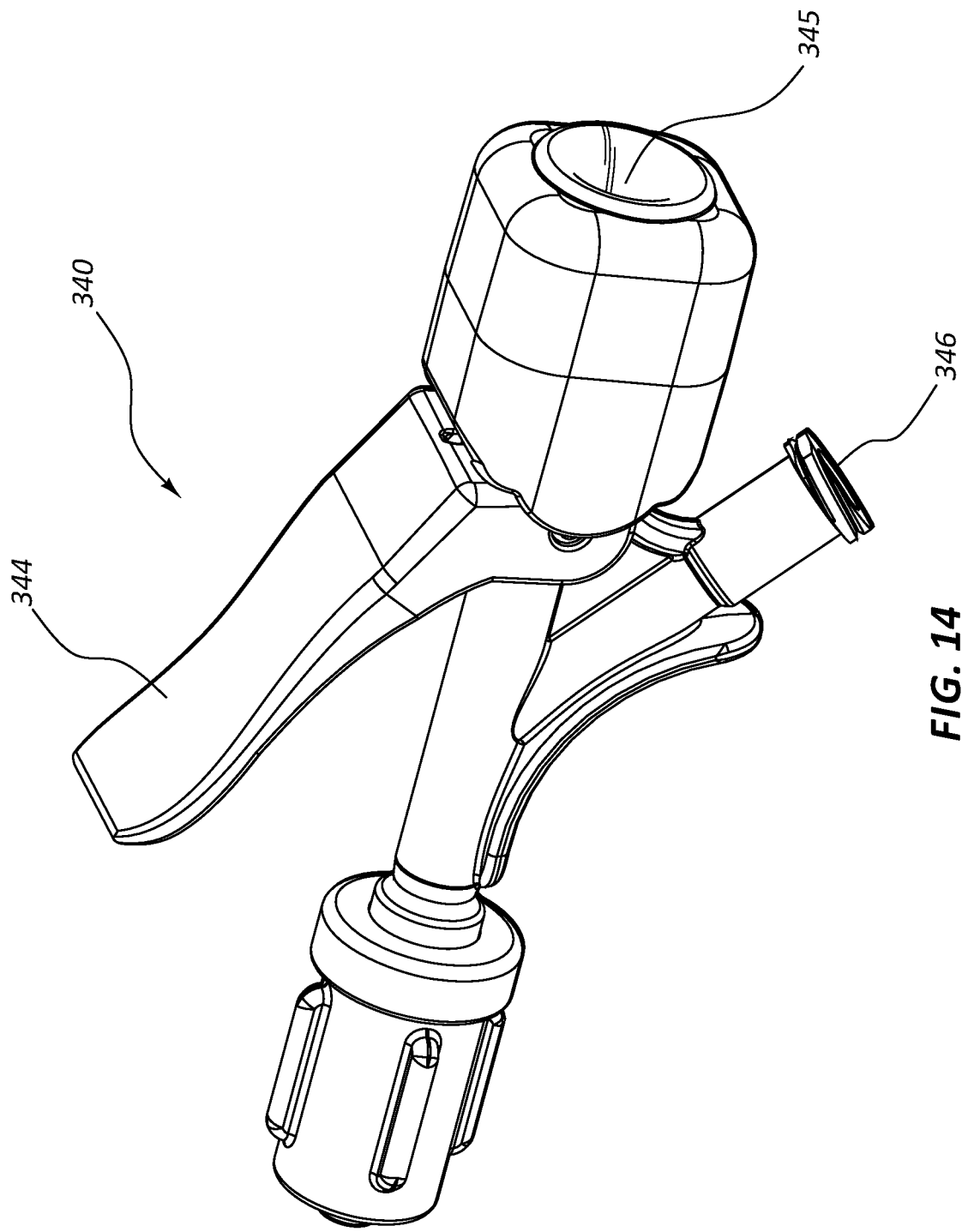
FIG. 14 is a perspective view of another embodiment of a valve.
Figure 15:
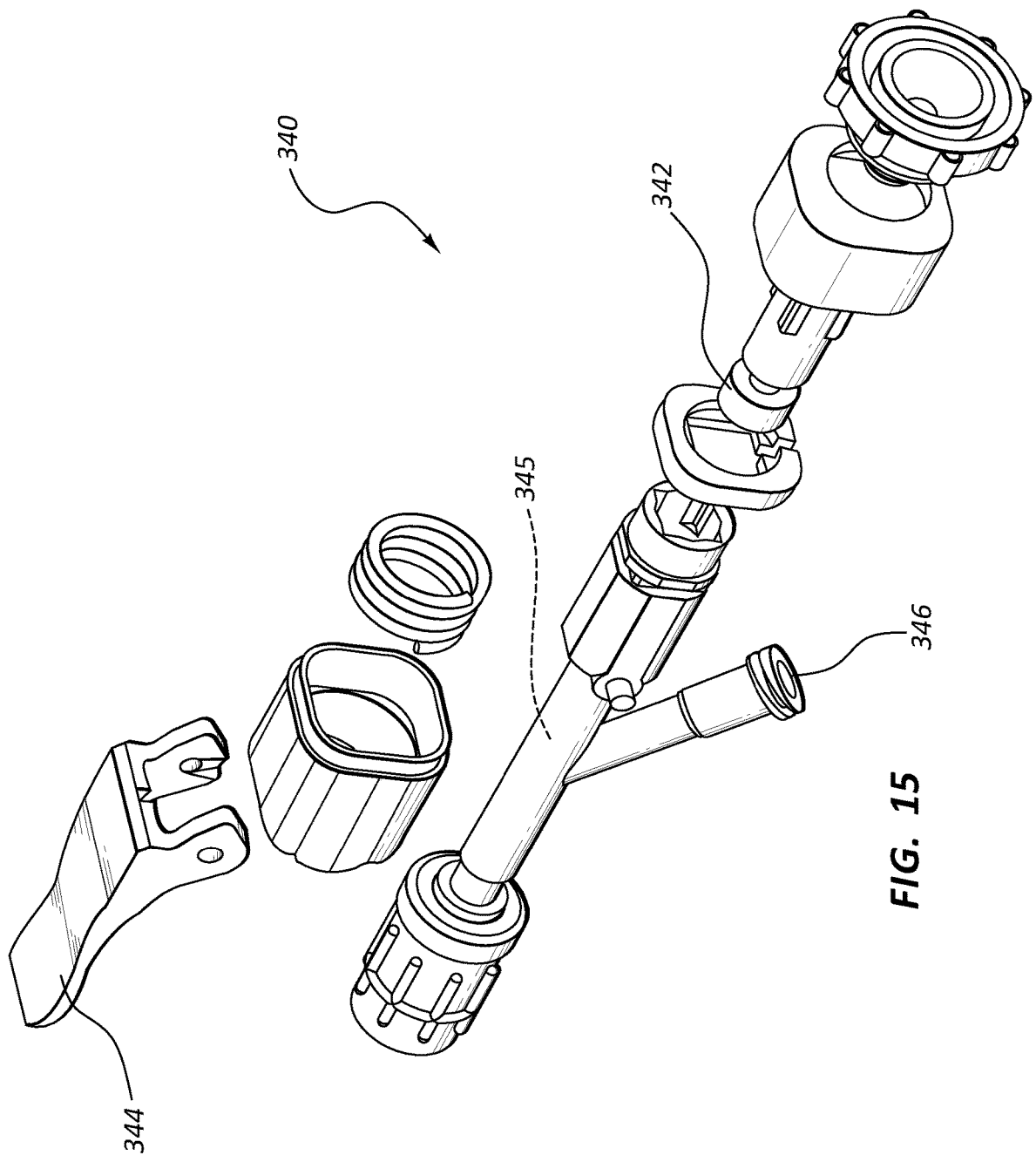
FIG. 15 is an exploded view of the valve of FIG. 14.
Figure 16:
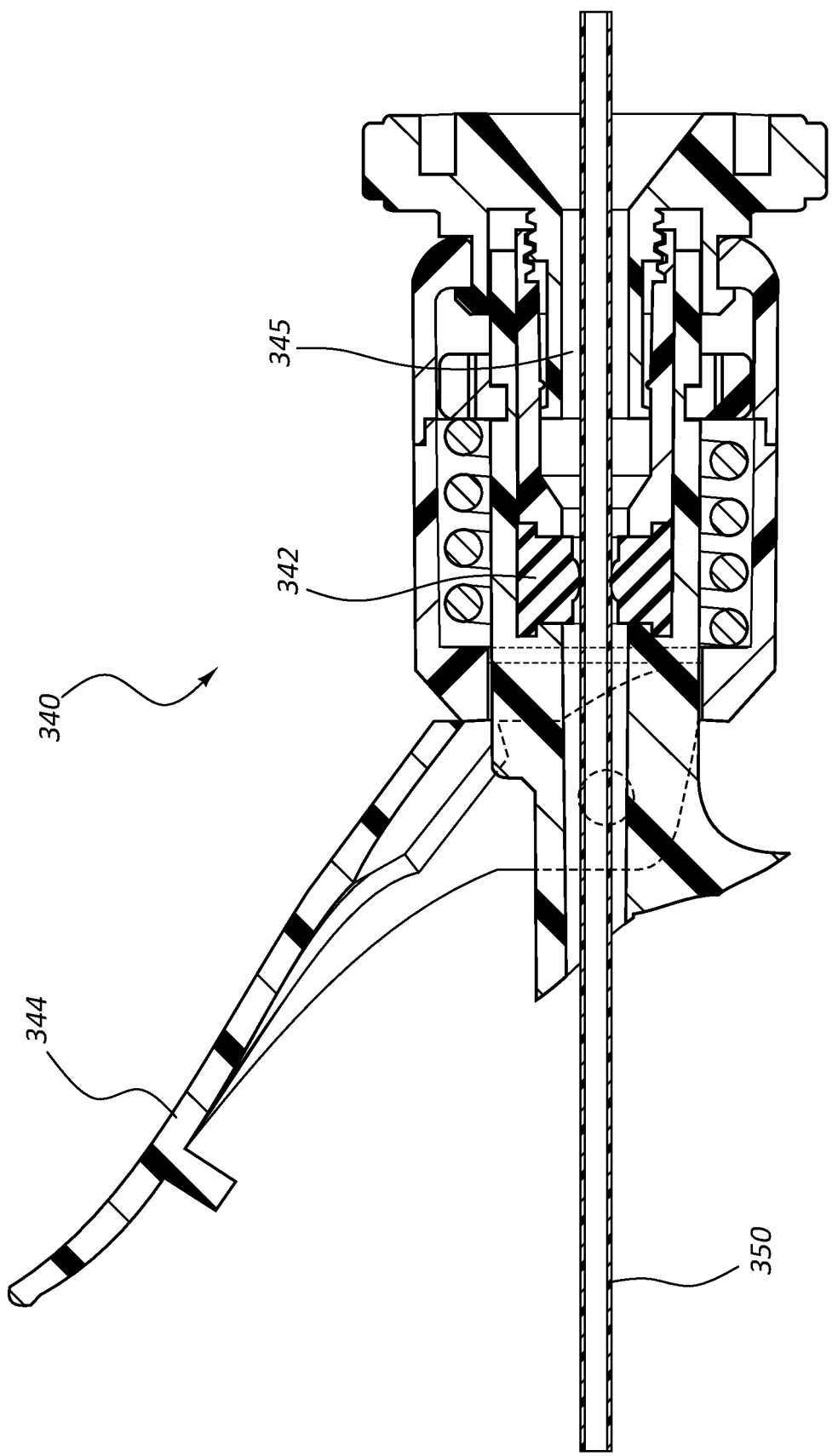
FIG. 16 is a cross-sectional view of a portion of the valve of FIG. 14 with an elongate device disposed therein.

FIG. 14 is a perspective view of another embodiment of a valve 340, FIG. 15 is an exploded view thereof, and FIG. 16 is a cross-sectional view of a portion thereof. FIG. 16 further includes an elongate device 350 disposed within a valve lumen 345 of the valve 340. The valve 340 of FIGS.

14-16 comprises a seal 342, an actuator 344, a valve lumen 345, and a side port 346. These components may function analogously to similarly indicated components of the valve 240 of FIG. 13.

The actuator 344 of the valve 340 of FIGS. 14-16 may be a lever, which may be biased in an extended position. Depressing the actuator 344 may open or close the seal 342 depending on the arrangement of internal components of the valve 340. For example, the seal 342 may be compressed in a closed position when the actuator 344 is extended and may open as the actuator 344 is depressed. A mechanism such as a lever actuator 344 may be configured to allow a practitioner to incrementally open or close the seal 342 by incrementally depressing the actuator 344. This may allow a practitioner to open the seal 342 just enough to facilitate displacement of an elongate device 350 within the valve lumen 345 without opening the seal 342 such that there is bleed back around the elongate device 350. The elongate device 350 may comprise, for example, a biopsy device, a catheter, a stent delivery device, or any other transvascular therapy device. In the cross-sectional view of FIG. 16, the seal 342 is closed about the elongate device 350 disposed in the valve lumen 345.

Figure 17:
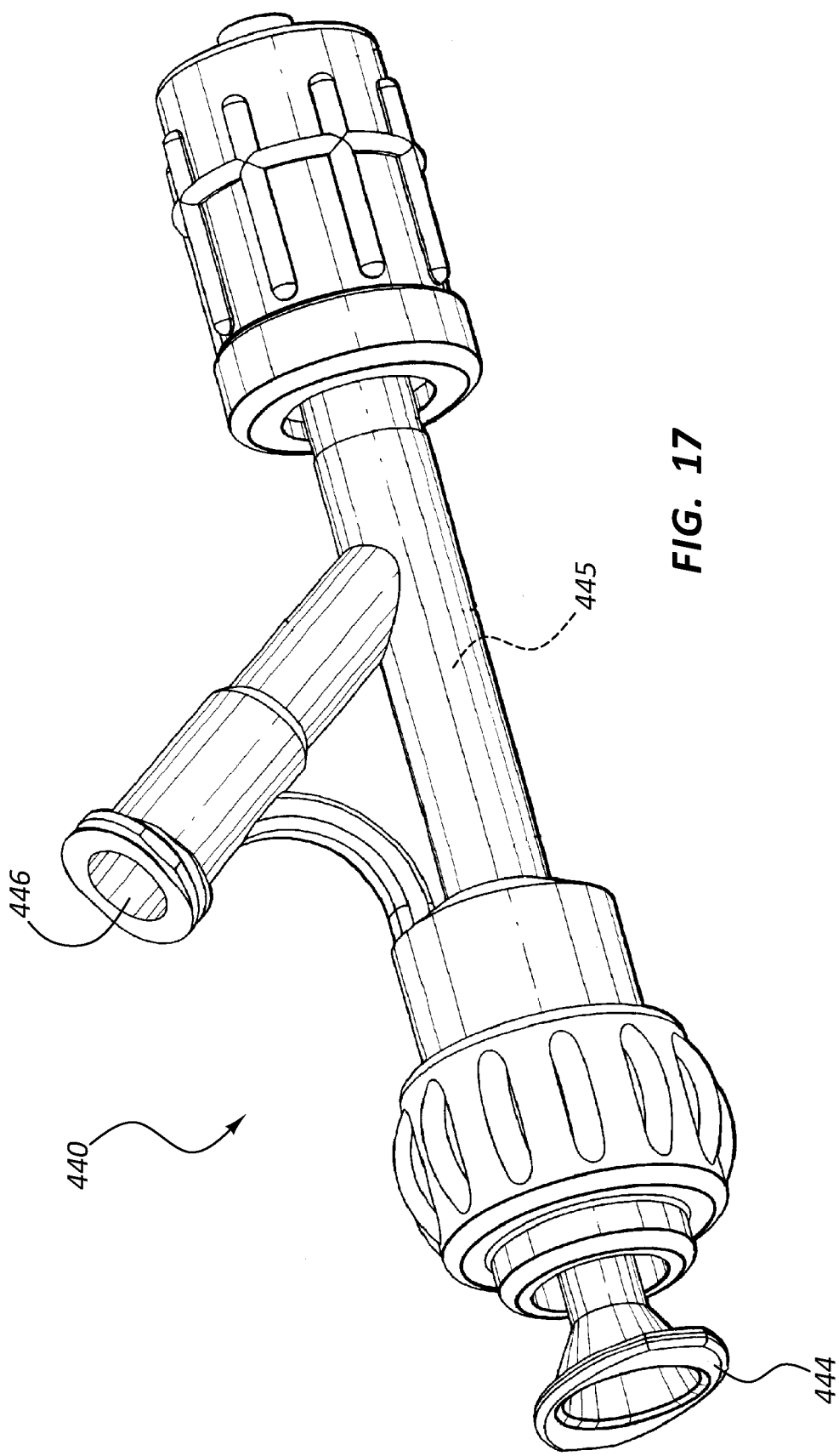
FIG. 17 is a perspective view of another embodiment of a valve.
Figure 18:
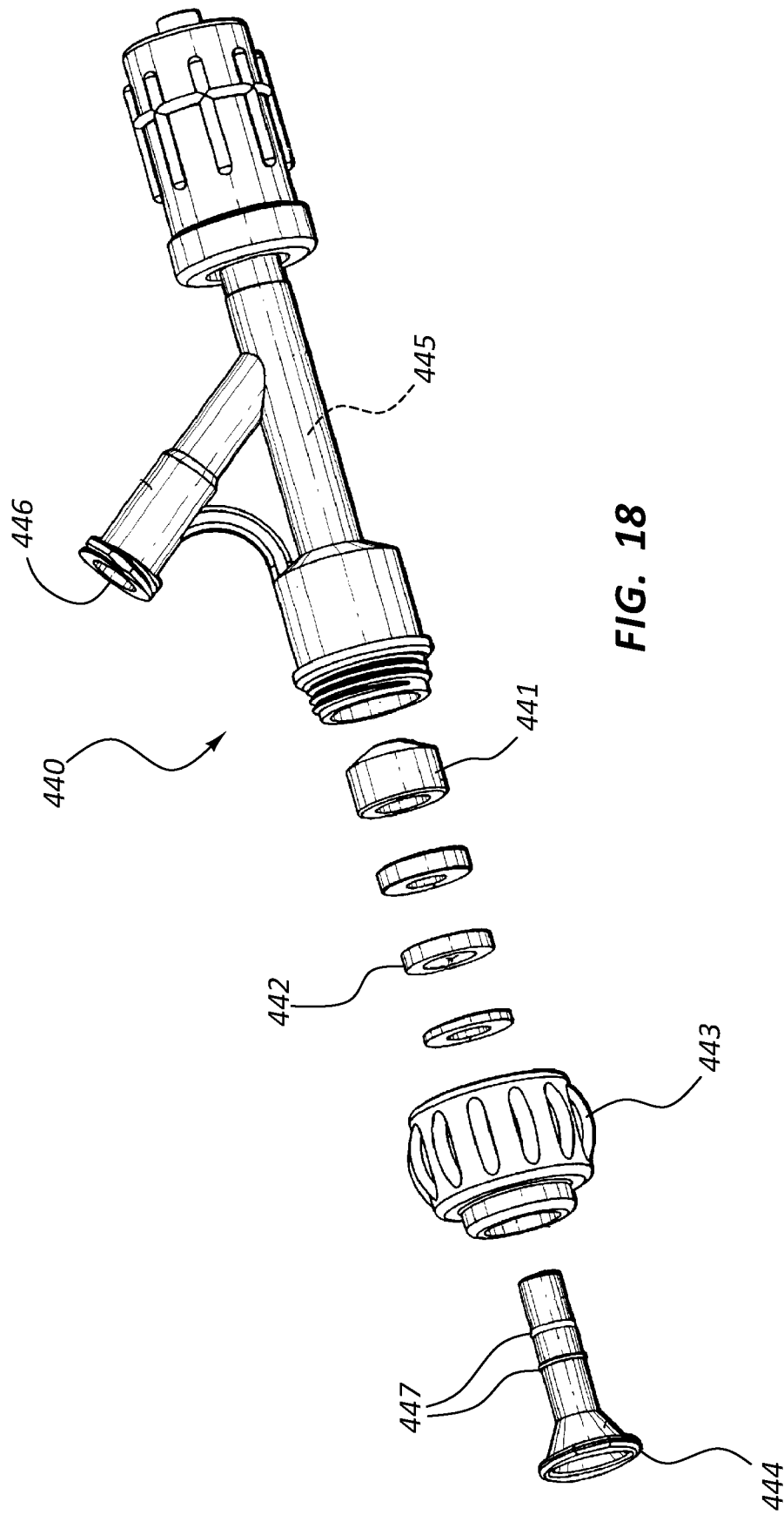
FIG. 18 is an exploded view of the valve of FIG. 17.
Figure 19:
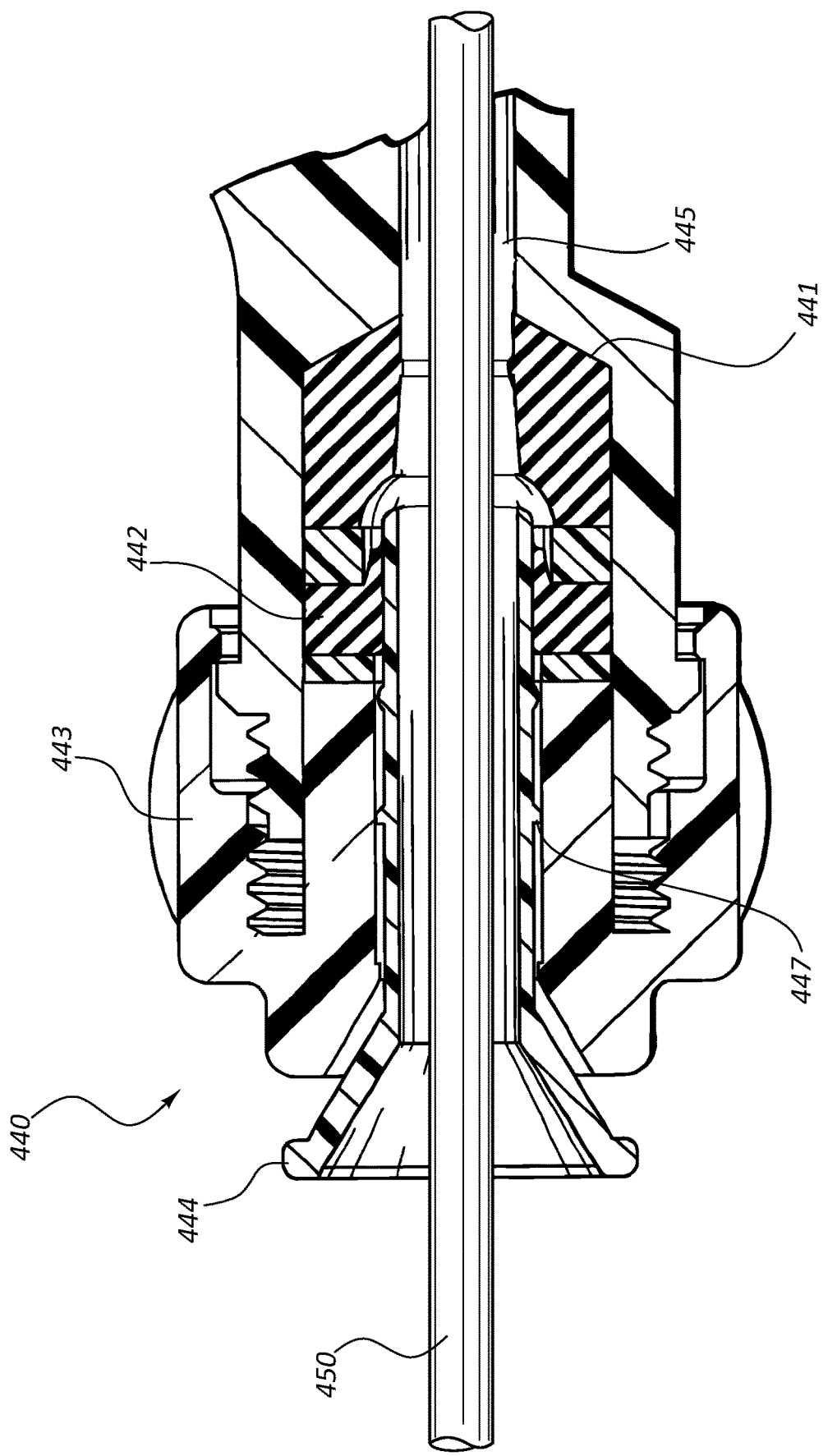
FIG. 19 is a cross-sectional view of a portion of the valve of FIG. 17 with an elongate device disposed therein.

FIG. 17 is a perspective view of another embodiment of a valve 440, FIG. 18 is an exploded view thereof, and FIG. 19 is a cross-sectional view of a portion thereof. FIG. 19 further includes an elongate device 450 disposed within a valve lumen 445 of the valve 440. The valve 440 of FIGS. 17-19 comprises a seal 442, an actuator 444, a valve lumen 445, and a side port 446. These components may function analogously to similarly indicated components of the valves 240, 340 of FIGS. 13-16.

The actuator 444 of the valve 440 of FIGS. 17-19 may be configured such that axially displacing the actuator 444 in a distal direction with respect to the seal 442 causes a distal portion of the actuator 444 to interact with the seal 442, forcing the seal 442 open. Retracting the actuator 444 in a proximal direction with respect to the seal 442 may remove the actuator 444 from contact with the seal 442, allowing the seal 442 to close. The actuator 444 may be configured to remain in the open or closed configuration whether or not the practitioner is applying a force to the actuator 444, or the actuator 444 may be biased in one position or the other.

The actuator 444 may be configured to provide an audible and/or tactile indication that the seal 442 has been opened and/or closed. For example, the actuator 444 may be configured with ridges 447 configured to interact with other portions of the valve 440. Features such as ridges 447 or other detents may be configured to maintain the position of the actuator 444 (and therefore the seal 442) and/or provide an audible or tactile indication that the seal 442 has been changed from one configuration to another.

The valve 440 of FIG. 18 may further comprise a rotary member 443. The rotary member 443 may be configured to interact with threads positioned on another portion of the valve 440 such that the rotational position of the rotary member 443 controls compressive forces acting on a conical member 441. The conical member 441 may be configured such that, when compressed, the conical member 441 tends to engage an elongate instrument disposed within the valve lumen 445. Thus, in some embodiments, compression of the conical member 445 couples such an instrument to the valve 440. This coupling may also act as a secondary seal, in connection with seal 442.

Any of the valves disclosed in any embodiment herein may comprise certain features described in connection with any other embodiment. For example, any of the valves may be configured to produce an audible and/or tactile indication of a change to the configuration of the valve. Other features of each embodiment may be analogously applied to the other embodiments.

Further, any of the valves described herein may be utilized in connection with any of the other components or assemblies described herein. Referring to FIG. 1, a valve 140 may be used in connection with a medical device assembly such as transvascular liver biopsy assembly 100. In one exemplary procedure, a practitioner may insert an introducer sheath 110 into a patient with the valve 140 in a closed configuration. The practitioner may then open the valve 140 and insert a biopsy assembly 150 into the introducer sheath 110. Once the biopsy assembly 150 is inserted, the practitioner may then close the valve 140. The assembly may then be rotated (for example, the introducer sheath 110 may be rotated in connection with the rotary indexer 130) or otherwise manipulated into a desired position or configuration. The biopsy assembly 150 may then be used to obtain a tissue sample, with the valve 140 still in the closed configuration. The valve 140 may then be disposed in the open configuration and the biopsy assembly 150 withdrawn. The valve 140 may again be closed. In other procedures, the configuration of the valve 140 may be other than that described, depending on the therapy or practitioner preference. For example, a practitioner may open the valve 140 when actuating a biopsy assembly 150 to obtain a sample or when manipulating the position of the assembly 100 or any component thereof. Further, a practitioner may advance or retract a component, such as biopsy assembly 150, with the valve 140 in a closed configuration, essentially pushing or pulling the component while in contact with a seal of the valve 140. Moreover, valves configured to toggle between the open and closed configurations without requiring a practitioner to maintain contact with an actuator, or valves biased in either the open or closed position (which change to the non-biased configuration only in response to continued input at an actuator) may each be used in connection with any of the procedures disclosed herein.

FIG. 20 is a side view of the biopsy assembly 150 of the assembly 100 of FIG. 1. The biopsy assembly 150 may comprise a handle 155 configured to manipulate, fire, or otherwise operate other components of the biopsy assembly 150, such as needles, trocars, stylets, cannulas, and so forth, in order to obtain a tissue sample. Any handle 155 shape, style, or design is within the scope of this disclosure. The biopsy assembly 150 of FIG. 20 further comprises a stylet 160 disposed within a cannula 170. The stylet 160 and cannula 170 may be operably coupled to handle 155 such that manipulation or actuation of the handle 155 is configured to advance or retract the stylet 160 and/or cannula 170 in order to obtain a tissue sample. The biopsy assembly 150 of FIG. 20, as well as any other biopsy assembly disclosed herein, may further comprise one or more outer sheath members (not shown), which may be disposed around the cannula 170 and/or stylet 160. An outer sheath member may be configured to deliver or protect the operative components and may be fixedly coupled to the handle 155.

FIG. 21 is an exploded perspective view of the stylet 160 and cannula 170 of the biopsy assembly 150 of FIG. 20. The stylet 160 may comprise a sharp distal end 162 configured to be advanced through tissue. A recessed trough 164 on the stylet 160 may be configured to isolate a tissue sample, which may be severed by the cannula 170. For example, and as further described below, the stylet 160 may be advanced into tissue such that the trough 164 of the stylet 160 extends beyond a distal tip 172 of the cannula 170. Tissue may prolapse into, or otherwise enter, the void formed by the trough 164. Tissue within the trough 164 may then be severed by the distal tip 172 of the cannula 170 as the cannula is distally advanced with respect to the stylet 160. A distal segment 174 of the cannula 170 may then retain the severed tissue within the trough 164. The stylet 160 and cannula 170 may then be retracted together to remove the severed tissue sample.

Referring to FIG. 1 and FIGS. 20-21, in some instances a biopsy assembly 150 may be configured to traverse an introducer sheath 110 or other path when positioning the distal tip 162 of the stylet 160 adjacent desired tissue within the body. The stylet 160 and cannula 170 may thus comprise elongate proximal segments 161, 171, respectively, configured to advance the distal tips 162, 172 of these components within the body. The proximal segments 161, 171 may operably connect the distal tips 162, 172 to the handle 155 while allowing the distal tips 162, 172 to be offset from the handle 155. The length of the proximal segments 161, 171 may be related to the therapy for which the biopsy assembly 150 is configured for use. For example, the biopsy assembly 150 may be configured for use in connection with a transjugular liver biopsy. In such instances, the proximal segments 161, 171 may be sized such that the handle 155 may be disposed proximally of the insertion site, while the distal tips 162, 172 are disposed adjacent liver tissue to be biopsied.

Referencing FIGS. 1 and 4, an introducer sheath 110 configured for use in connection with a biopsy assembly 150 may comprise a curved distal tip 112. The biopsy assembly 150 may comprise flexible segments configured to traverse the curvature of the curved distal tip 112.

Referring again to the biopsy assembly 150 of FIGS. 20-21, the stylet 160 and cannula 170 may each comprise a flexible segment 166, 176 disposed distally of the proximal segments 161, 171 of each component. The flexible segments 166, 176 may be configured to traverse a curved path and/or be disposed in a curved path when the biopsy assembly 150 is in use. Operative segments or segments configured to isolate, sever, or contain tissue samples (such as distal tip 162, trough 164, distal tip 172, and distal segment 174) may be disposed distally of the flexible segments 166, 176. In other embodiments, any of these components may be configured with multiple flexible segments disposed at various locations in order to facilitate use of the biopsy assembly 150 across delivery paths comprising multiple bends or curves.

Figure 22:
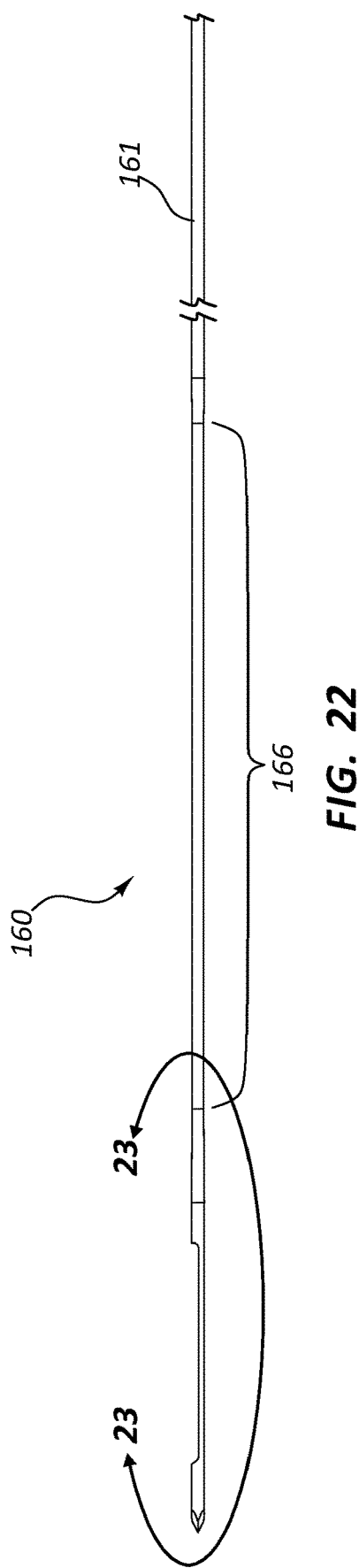
FIG. 22 is a side view of the stylet of the biopsy assembly of FIG. 20.
Figure 23:
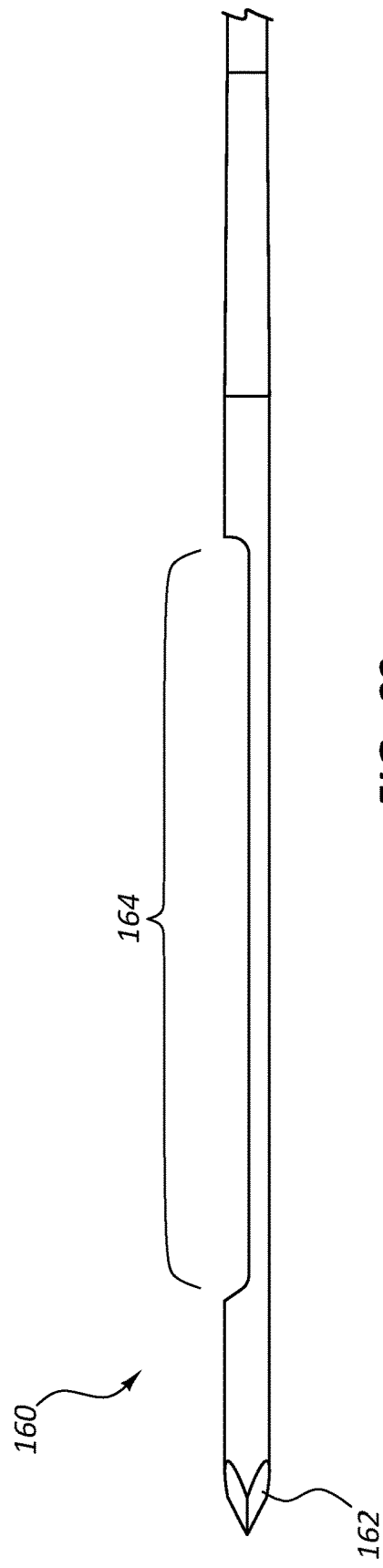
FIG. 23 is an enlarged view of a portion of the stylet of FIG. 22, taken around line 23-23.

FIG. 22 is a side view of the stylet 160 of the biopsy assembly 150 of FIG. 20, and FIG. 23 is an enlarged view of a portion of the stylet 160 of FIG. 22, taken around line 23-23. FIGS. 22 and 23 illustrate a portion of the proximal segment 161 of the stylet 160, as well as the flexible segment 166, the trough 164, and the sharp distal tip 162. In some embodiments, the stylet 160 may be generally formed of an elongate member having a generally circular cross-section. Certain features, such as the trough 164, may be formed by removing material from the generally circular member. The flexible segment 166 may be formed by grinding or otherwise removing material such that the flexible segment 166 has a smaller outside diameter than the proximal segment 161. The stylet 160 may comprise tapered or transition zones between the smaller-diameter flexible segment 166 and the proximal segment 161 and/or the operative distal end of the stylet 160. In some embodiments, the flexible segment 166 may have a generally circular cross-section. In other embodiments, the flexible segment 166 may have a cross-section other than a circular cross-section, including in embodiments where the proximal segment 161 has a generally circular cross-section.

Various elongate members, which may be configured to be passed through a sheath, are discussed herein. (For example: stylet 160 of FIGS. 22-23, cannula 170 of FIGS. 24 and 25, analogous stylets—such as 760 of FIG. 36—and analogous cannula—such as 770 of FIG. 36—of other embodiments, and the outer tubular member 780 of FIG. 36). Any of these elongate instruments may be configured with a flexible segment. In some such embodiments, the flexible segment may be characterized as more flexible than another portion of the elongate instrument, such as a portion of the instrument disposed proximally or distally of the flexible segment. For example, a flexible segment may be more flexible than an operative segment disposed distally of the flexible segment. In some instances, the apparent bending modulus of the segments may be used to compare relative flexibilities. Further, in some embodiments, the relative flexibility of various segments may be determined by measuring the force required to deflect portions of identical lengths an identical amount. In some instances, the force required to deflect a length of a flexible segment a particular amount is an order of magnitude less than the force required to deflect a stiffer segment (either proximal or distal) having the same length, the same amount.

Figure 24:
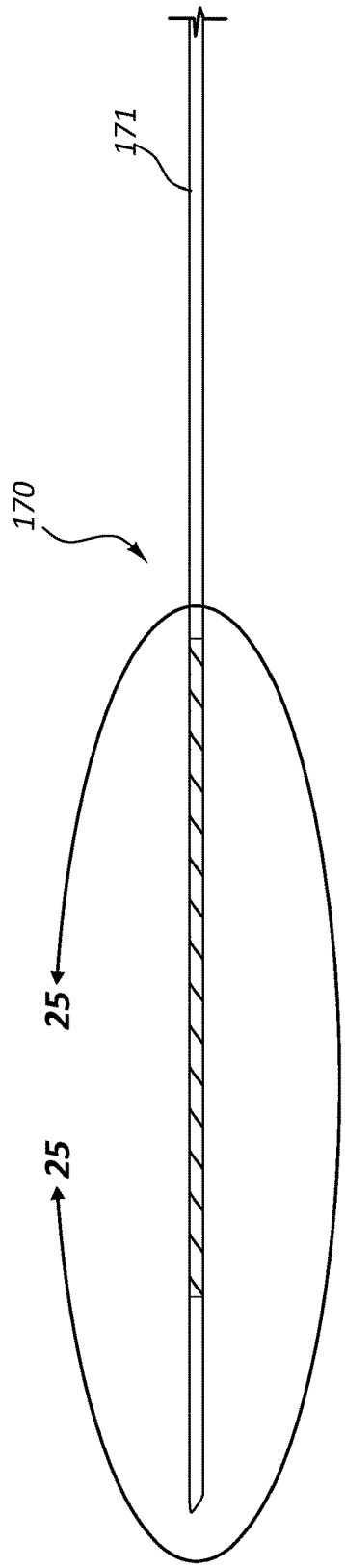
FIG. 24 is a side view of the cannula of the biopsy assembly of FIG. 20.
Figure 25:
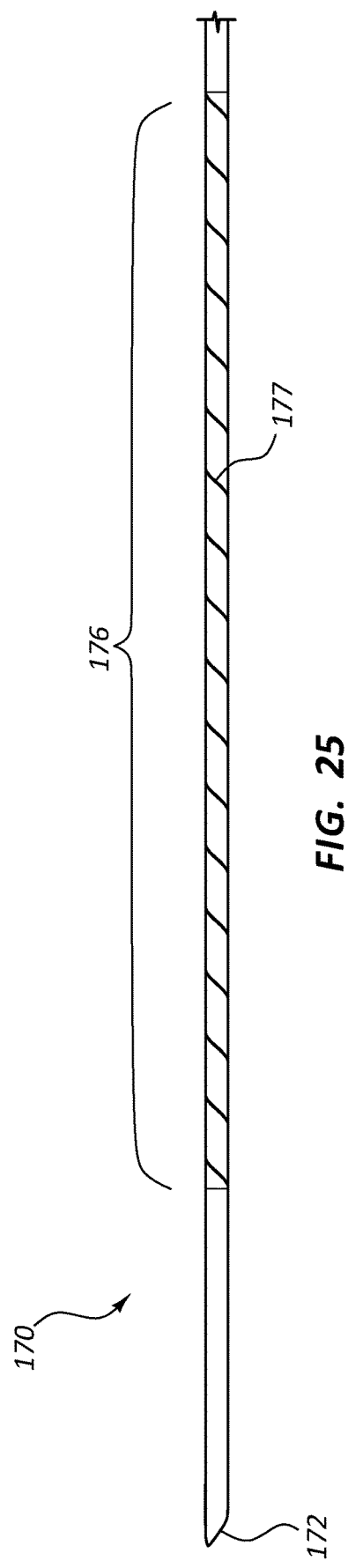
FIG. 25 is an enlarged view of a portion of the cannula of FIG. 24, taken around line 25-25.

FIG. 24 is a side view of the cannula 170 of the biopsy assembly 150 of FIG. 20. FIG. 25 is an enlarged view of a portion of the cannula 170 of FIG. 24, taken around line 25-25. FIGS. 24 and 25 illustrate the proximal segment 171 of the cannula 170, as well as the flexible segment 176 and the distal tip 172. In some embodiments, the cannula 170 may comprise a generally hollow member. The flexible segment 176 may be formed by creating a spiral cut 177 in the wall of the hollow member. The spiral cut 177 may extend completely through a wall of the hollow member, from the outside diameter to the inside diameter. The spiral cut 177 may extend in one continuous helix along the flexible segment 176, or may be comprised of multiple cuts extending along certain portions of the flexible segment 176. Spiral cuts described in connection with this or any other embodiment here may be formed by laser cutting, grinding, mechanical cutting, or any other method.

Flexible segments, such as segment 166 of FIG. 22 and segment 176 of FIG. 25, may be positioned at various points along members of any biopsy device or similar device within the scope of this disclosure. Any disclosure provided herein in connection with the flexible segment of a solid member (such as flexible segment 166 of FIG. 22) may be applied to any other elongate solid member of any embodiment of a biopsy device or other medical device. Similarly, any disclosure provided herein in connection with the flexible segment of a hollow member (such as the flexible segment 176 of FIG. 25) may be applied to any other elongate hollow member of any embodiment of a biopsy device or other medical device.

Figure 26:
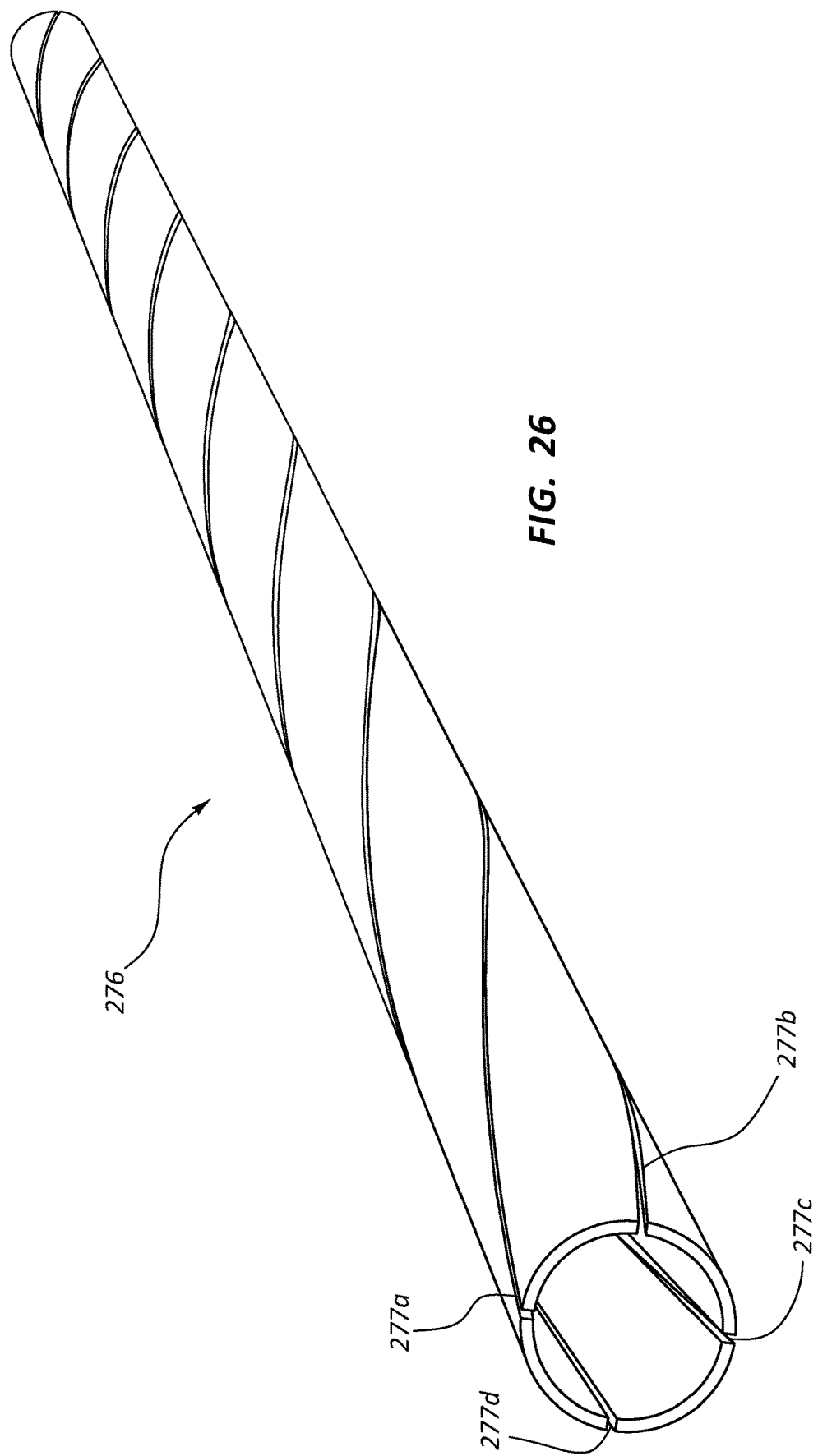
FIG. 26 is a side view of another embodiment of a flexible segment of a component of a biopsy assembly.

FIG. 26 is a side view of another embodiment of a flexible segment 276 of a component of a biopsy assembly. As with disclosure relative to other flexible segments, any disclosure provided in connection with this embodiment is applicable to any hollow member of any elongate device. In the embodiment of FIG. 26, the flexible segment 276 comprises four spiral cuts 277a, 277b, 277c, 277d extending from an outside diameter to an inside diameter of the flexible segment 276. The spiral cuts 277a, 277b, 277c, 277d may be disposed such that the cuts do not cross each other, or may be disposed to cross at certain points. The cuts 277a, 277b, 277c, 277d may or may not be substantially parallel along the length of the cuts 277a, 277b, 277c, 277d. While the illustrated embodiment comprises four spiral cuts, other embodiments may comprise one, two, three, five, six, seven, eight, or any other number of spiral cuts. Further, certain embodiments may have segments of a different number of cuts at different points along the length of the flexible segment. For example, a flexible segment may have one spiral cut that runs the entire length of the flexible segment and additional spiral cuts that only extend along a portion of the length of the flexible segment.

Figure 27:
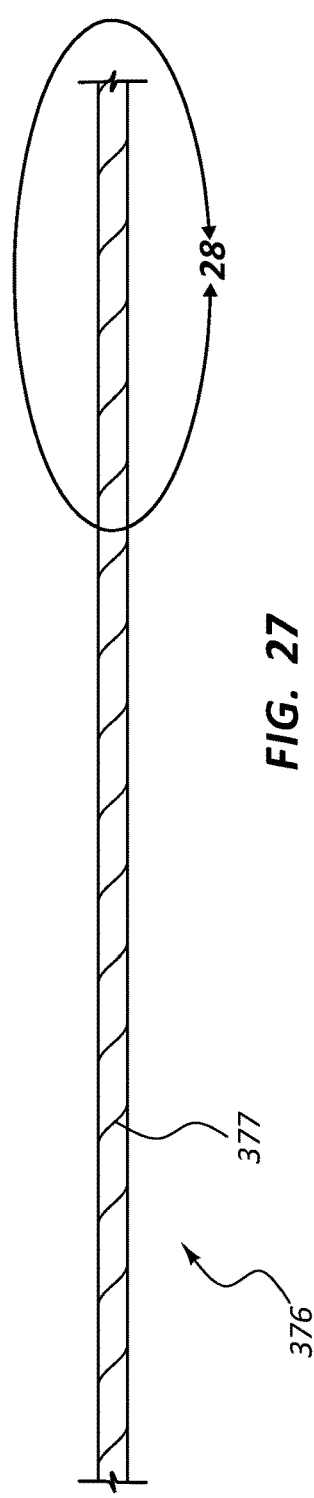
FIG. 27 is a side view of another embodiment of a flexible segment of a component of a biopsy assembly.
Figure 28:
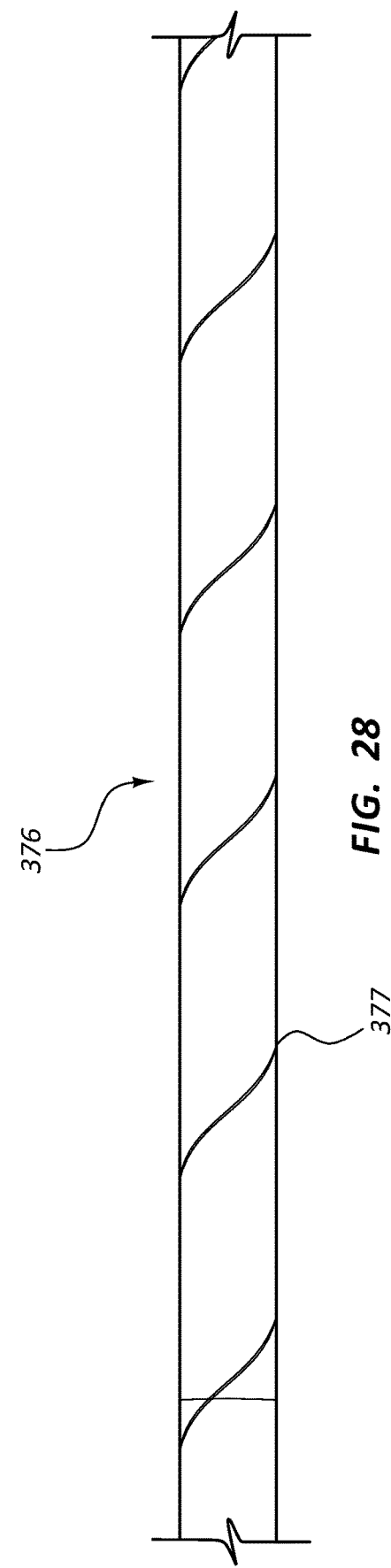
FIG. 28 is an enlarged view of a portion of the flexible segment of FIG. 27, taken around line 28.

FIG. 27 is a side view of another embodiment of a flexible segment 376 of a component of a biopsy assembly. FIG. 28 is an enlarged view of a portion of the flexible segment 376 of FIG. 27, taken around line 28. In the illustrated embodiment, the flexible segment 376 comprises one spiral cut 377 extending the entire length of the flexible segment 376. In the illustrated embodiment, the spiral cut 377 is configured with a constant pitch along the entire length of the flexible segment 376. The pitch may be from about four revolutions per inch to about ten revolutions per inch, including about five, six, seven, eight, or nine revolutions per inch or any partial number in the range, such as 7.5 revolutions per inch.

FIG. 29 is a side view of another embodiment of a flexible segment 476 of a component of a biopsy assembly. FIG. 30 is an enlarged view of a portion of the flexible segment 476 of FIG. 29, taken around line 30-30. FIG. 31A is an enlarged view of a portion of the flexible segment 476 of FIG. 30, taken around line 31A. In the embodiment of FIGS. 29-31A, a spiral cut 477 in the flexible segment 476 comprises a transition portion 478. In the illustrated embodiment, the pitch of the spiral cut 477 is not constant in the transition portion 478. Rather, it transitions from no pitch (or aligned with a longitudinal axis of the flexible segment 476) to a pitch about the flexible segment 476. Thus, in some embodiments, a spiral cut may begin at an end of the flexible segment 476 with very little or no pitch. The spiral cut 477 may then transition to a constant pitch, continuously vary along the length of the flexible segment 476, or vary for portions and remain constant for portions of the flexible segment 476. A spiral cut 477 with a transition portion 478 having a shallow pitch disposed at an end of the flexible segment 476 may be configured to reduce stress concentrations at the end of the flexible segment 476. A flexible segment may have a transition portion 478 at a distal end of the flexible segment, the proximal portion of the flexible segment, or both. Flexible segments having multiple spiral cuts may also be configured with a transition portion or other segment of non-constant pitch.

The embodiment of FIGS. 29-31A further comprises struts 479 disposed along the length of the spiral cut 477. The struts 479 may comprise small portions of the member which are not removed to form the spiral cut 477. The struts 479 may be configured to transfer longitudinal forces along the length of the flexible segment 476 while still increasing the flexibility of the flexible segment 476 with a spiral cut 477.

FIG. 31B is an enlarged view of another embodiment of a portion of a flexible segment, analogous to the view of FIG. 31A, showing another embodiment of a strut. FIG. 31C is an enlarged view of a portion of FIG. 31B. In the embodiment of FIGS. 31B and 31C, the strut comprises a socket portion 479a and a ball portion 479b. These components may be disposed to provide a strut structure which may flex along and around the strut itself. In some embodiments, a top portion of the ball portion 479b may be removed, such that the top of the ball portion 479b does not contact the socket portion 479a when the flexible portion is compressed along its axis. Rather, opposing sides of the spiral cut itself (such as 477 of FIG. 30) may contact each other to bear a compressive force. This design may prevent the ball portion 479b from being easily deformed in response to compressive forces. Struts that comprise a socket portion 479a and a ball portion 479b may be configured to transfer longitudinal forces along the length of a flexible segment.

Some spiral cuts may be configured with no struts, some may comprise only struts such as that illustrated in FIG. 31A, others comprise only struts such as that shown in FIGS. 31B and 31C, while other embodiments comprise struts of both varieties at various points along a spiral cut.

Figure 32:
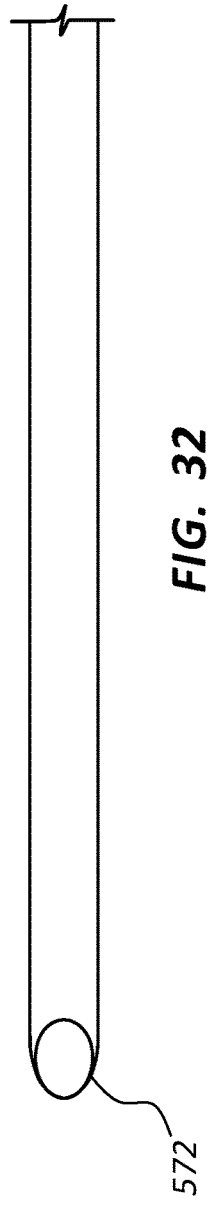
FIG. 32 is a top view of a portion of an operative segment of another embodiment of a portion of a biopsy assembly.
Figure 33:
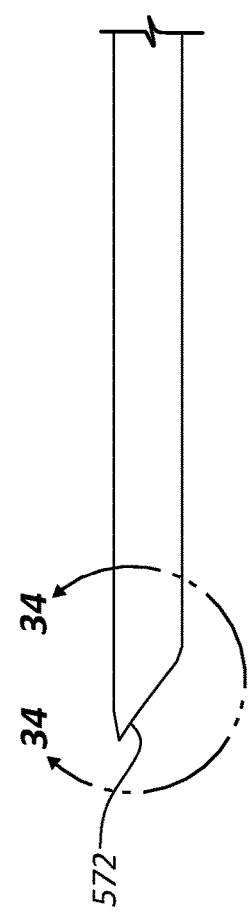
FIG. 33 is a side view of a portion of the operative segment of FIG. 32.
Figure 34:
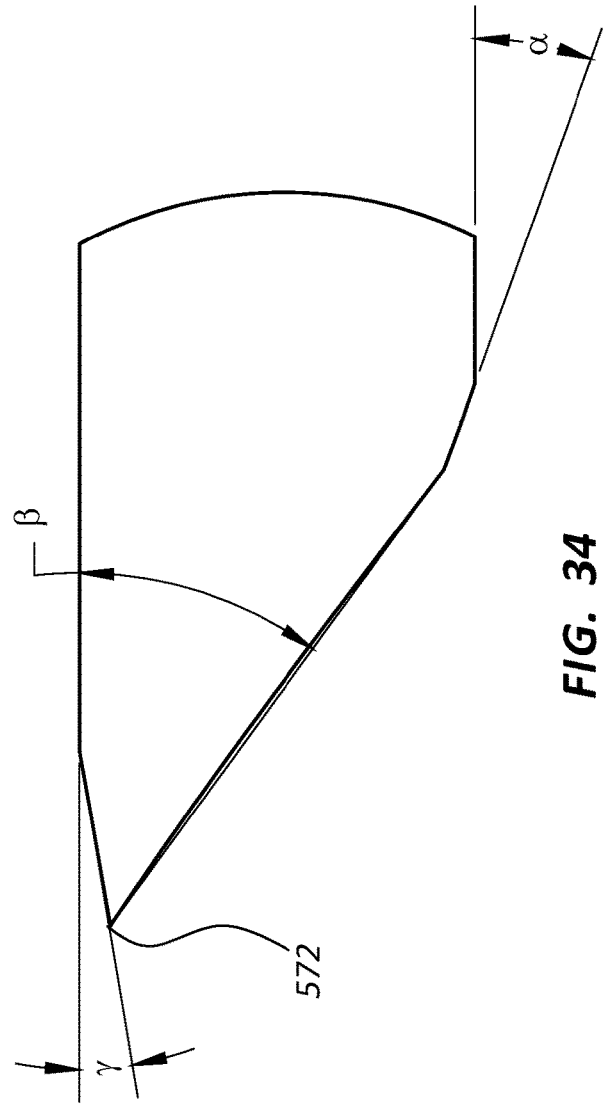
FIG. 34 is an enlarged view of the portion of the operative segment of FIG. 32, taken around line 34-34.

FIG. 32 is a top view of a portion of an operative segment of another embodiment of a portion of a biopsy assembly; FIG. 33 is a side view of a portion of the operative segment of FIG. 32; and FIG. 34 is an enlarged view of the portion of the operative segment of FIG. 33, taken around line 34-34. In the illustrated embodiment, features of a sharpened distal tip 572 of a hollow biopsy device member are shown. The sharpened distal tip 572 may be configured to sever a tissue sample disposed within a recessed trough (such as trough 164 of FIG. 23). The sharpened distal tip 572 may be configured both to sever the longitudinal length of the tissue sample and to interact with a distal end of a trough (such as trough 164 of FIG. 23) to sever the distal end of the sample.

Various angles are illustrated in FIG. 34. These angles may vary in various embodiments. For example, angle α may vary from about 8 degrees to about 11 degrees, angle β from about 33 degrees to about 39 degrees, and angle γ from about 18 degrees to about 21 degrees.

Figure 35A:
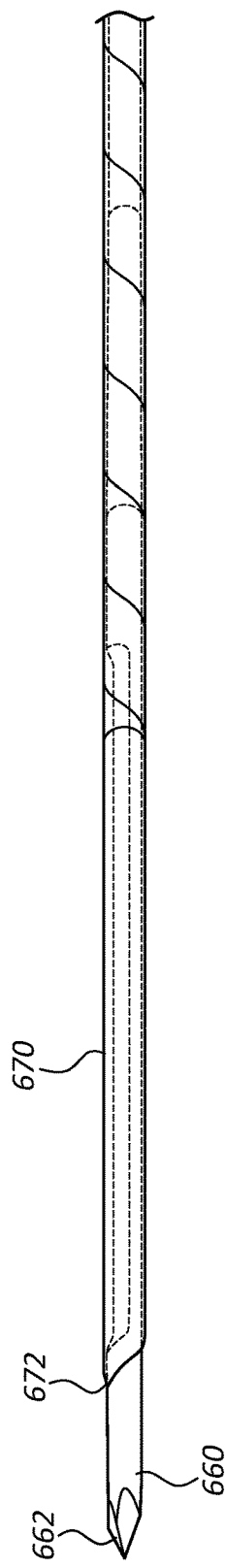
FIG. 35A is a side view of a portion of a biopsy assembly in a first configuration.
Figure 35B:
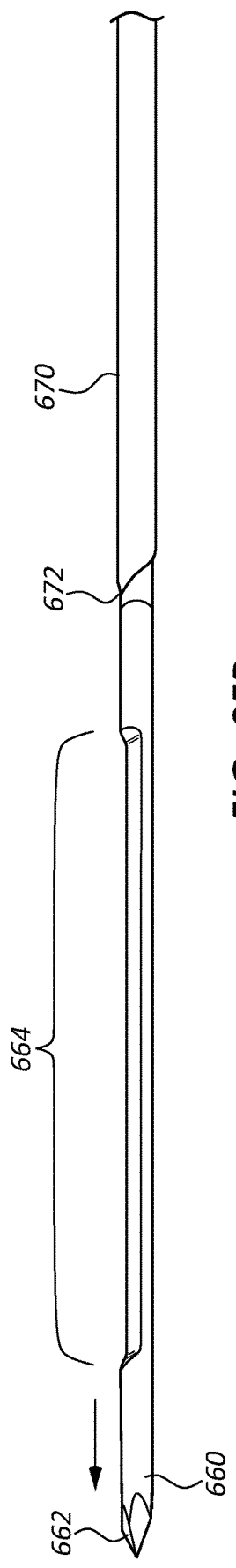
FIG. 35B is a side view of the biopsy assembly of FIG. 35A in a second configuration.
Figure 35C:
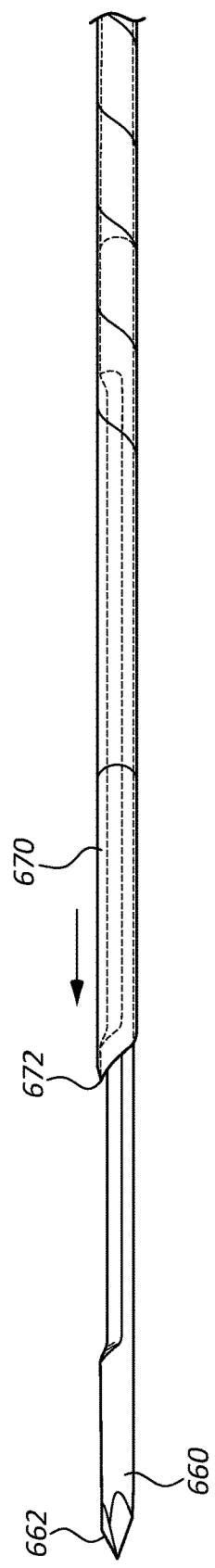
FIG. 35C is a side view of the biopsy assembly of FIG. 35A in a third configuration.

FIGS. 35A-35C are side views of a portion of a biopsy assembly in a first configuration, a second configuration, and a third configuration, respectively. The biopsy assembly may be operated by first advancing the device in the configuration of FIG. 35A to a position within the body adjacent a site to be biopsied. The device may be advanced through an introducer sheath (such as introducer sheath 110 of FIG. 4), including transjugular procedures wherein the introducer sheath is introduced to the vasculature at the jugular vein. In some such procedures, the biopsy device may be positioned adjacent a portion of the liver to be biopsied. In some such embodiments, flexible segments (such as 166 and 176 of FIGS. 22 and 25) may be disposed in a curved portion of the introducer sheath (such as curved distal tip 112 of FIG. 4) when the sample is obtained. The illustrated embodiment comprises a stylet 660 having a distal end 662 and a recessed trough 664. The illustrated embodiment further comprises a cannula 670 which may be disposed over stylet 660. The cannula 670 may comprise a sharpened distal tip 672.

In some embodiments, the sample may be obtained by advancing the stylet 660 with respect to the cannula 670 such that the distal tip 662 of the stylet 660 and the trough 664 extend beyond the distal tip 672 of the cannula 670, as shown in FIG. 35B, and into the tissue to be biopsied. Tissue may then prolapse into the recessed trough 664 of the stylet 660. The cannula 670 may then be advanced such that the distal tip 672 of the cannula 670 severs the length of the sample (along the length of the trough 664) and the distal end of the sample by interaction with the distal end of the trough 664, as shown in FIG. 35C. In some embodiments the biopsy assembly may be configured with springs or other mechanisms such that the components displace to obtain the sample automatically when the device is actuated.

Figure 36:
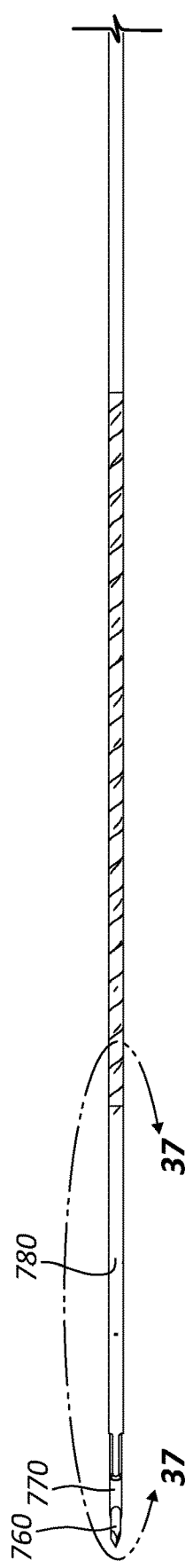
FIG. 36 is a top view of a portion of another embodiment of a biopsy assembly.

FIG. 36 is a top view of a portion of another embodiment of a biopsy assembly. The biopsy assembly of FIG. 36 comprises a stylet 760, a cannula 770, and an outer tubular member 780. In the embodiment of FIG. 36, and as further described below, the cannula 770 and outer tubular member 780 may be configured to sever a tissue sample. Any of the disclosure above relating to any other biopsy device, including the positioning and function of flexible segments, may be applicable to biopsy devices with a cannula 770 and outer tubular member 780 such as in FIG. 36.

Figure 37:
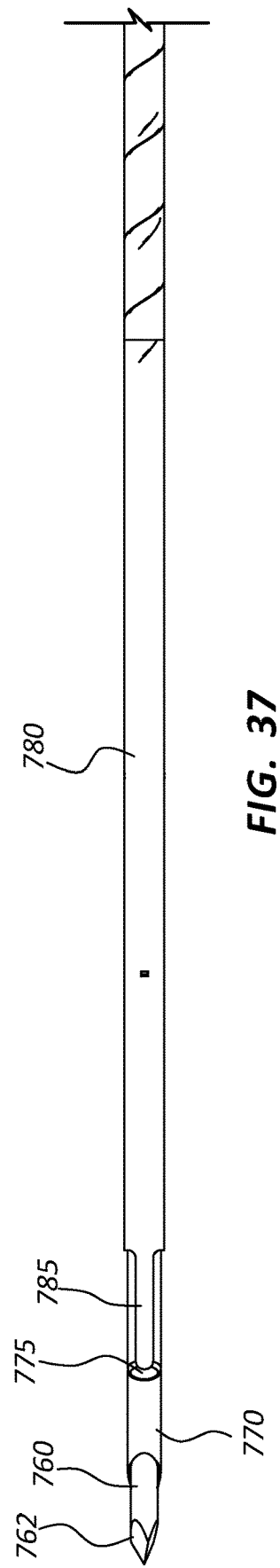
FIG. 37 is an enlarged view of a portion of the biopsy assembly of FIG. 36, taken around line 37-37.

FIG. 37 is an enlarged view of a portion of the biopsy assembly of FIG. 36, taken around line 37-37. As shown in FIG. 37, the stylet 760 may comprise a sharpened distal tip 762. The cannula 770 may comprise an opening 775 configured to receive a cutting member 785 coupled to the outer tubular member 780.

Figure 38:
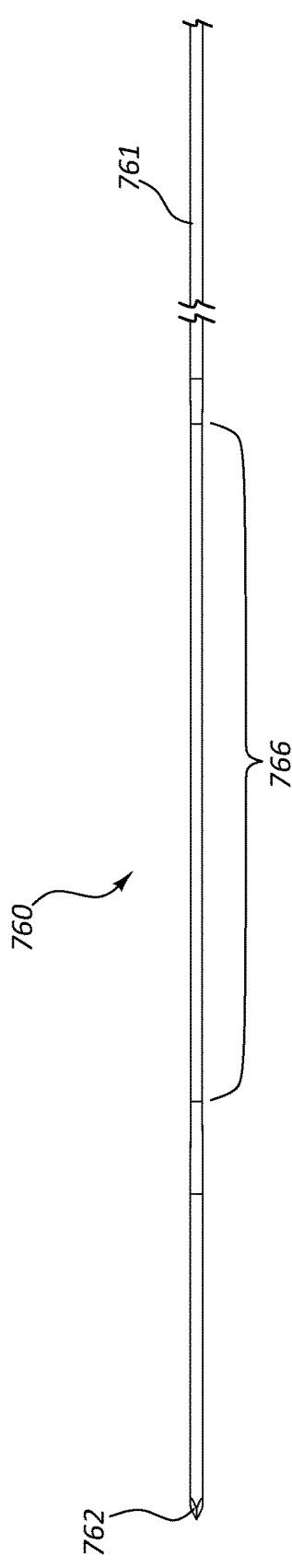
FIG. 38 is a side view of a portion of the stylet of the biopsy assembly of FIG. 36.

FIG. 38 is a side view of a portion of the stylet 760 of the biopsy assembly of FIG. 36. In the illustrated embodiment, the stylet 760 comprises a sharpened distal tip 762, a proximal segment 761, and a flexible segment 766. As with the stylets of other embodiments, the stylet 760 may comprise a generally solid circular member wherein the diameter of the flexible segment 766 is smaller than the diameter of the proximal segment 761. Unlike the stylets of earlier embodiments, the stylet 760 may not comprise a recessed trough, because in the embodiment of FIGS. 36-46D, the cannula 770 and outer tubular member 780 interact to isolate and sever a tissue sample.

Figure 39:
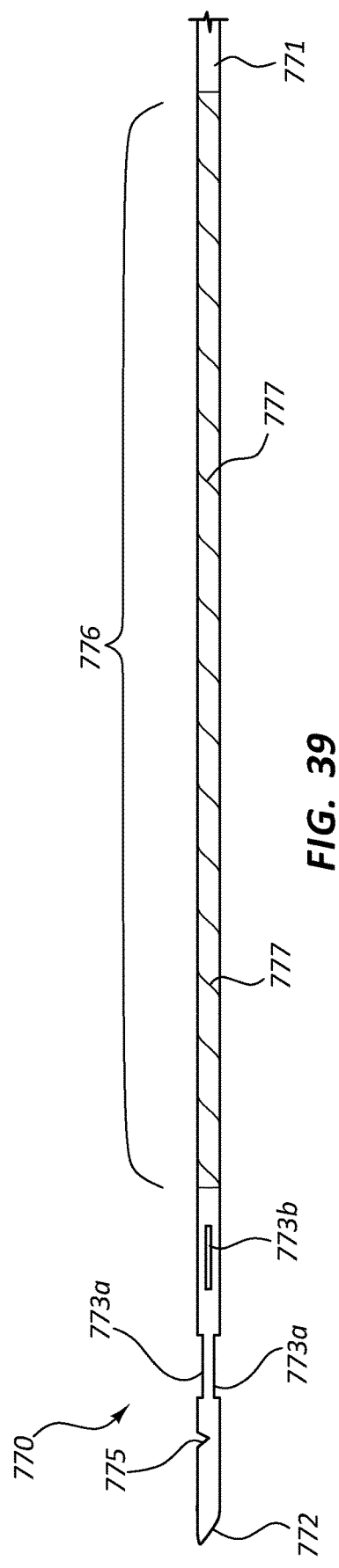
FIG. 39 is a side view of a portion of the cannula of the biopsy assembly of FIG. 36.

FIG. 39 is a side view of a portion of the cannula 770 of the biopsy assembly of FIG. 36. The cannula 770 comprises a sharpened distal tip 772, a flexible segment 776, and a proximal segment 771 which may be less flexible than the flexible segment 776. The cannula 770 may comprise a generally hollow member, and the flexible segment 776 may comprise a spiral cut 777 extending between the inside diameter and the outside diameter of the member. Any spiral cut arrangement disclosed herein may be applied to the cannula 770 of this embodiment or any other hollow member of this embodiment, such as the outer tubular member (780 of FIG. 40), for example.

The cannula 770 may also comprise an opening 775 and slots 773a, 773b configured to interact with the outer tubular member (780 of FIG. 40) as further disclosed below. The slots 773a, 773b, opening 775 and other features of the cannula 770 or other elongate members (such as the tabs 783a, 783b or cutting member 785 of the outer tubular member 780 of FIG. 40) are not necessarily drawn to scale for illustrative purposes.

Figure 40:
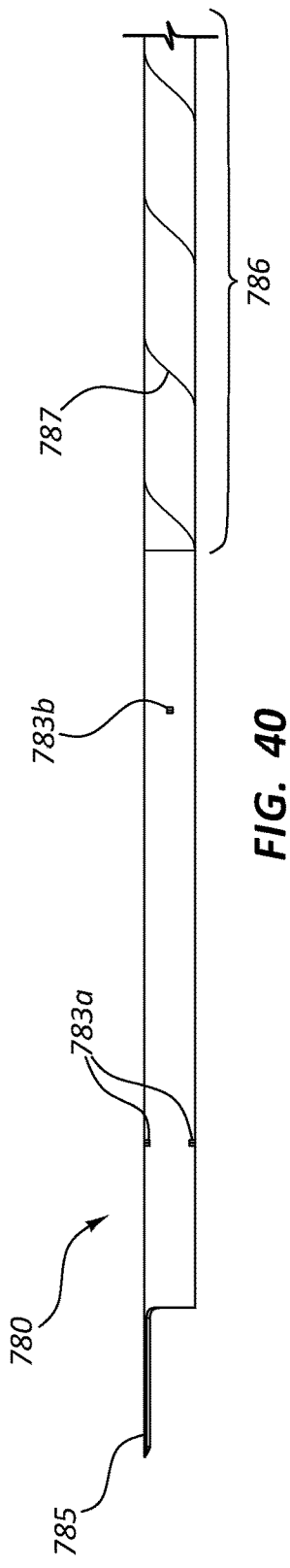
FIG. 40 is a side view of the outer tubular member of the biopsy assembly of FIG. 36.

FIG. 40 is a side view of the outer tubular member 780 of the biopsy assembly of FIG. 36. The outer tubular member 780 may comprise a cutting member 785 and a flexible segment 786 which may comprise a spiral cut 787. A proximal segment (not shown), which may be less flexible than the flexible segment 786, may be disposed proximally of the flexible segment 786. The outer tubular member 780 may also comprise a tabs 783a, 783b configured to interact with a slots (773a, 773b of FIG. 39) as further described below.

FIG. 41 is a side view of a portion of the biopsy assembly of FIG. 36; FIG. 42 is a cross-sectional view of the portion of the biopsy assembly of FIG. 41, taken through plane 42-42; and FIG. 43 is a cross-sectional view of the portion of the biopsy assembly of FIG. 41, taken through plane 43-43. The stylet 760, the cannula 770, and the outer tubular member 780 are shown in these views. The stylet 760 may be disposed within the cannula 770, and the outer tubular member 780 may be disposed around the cannula 770. The sharpened distal tip 762 of the stylet 760, the opening 775 of the cannula 770, and the cutting member 785 and tabs 783a, 783b of the outer tubular member 780 are also shown.

Figure 45:
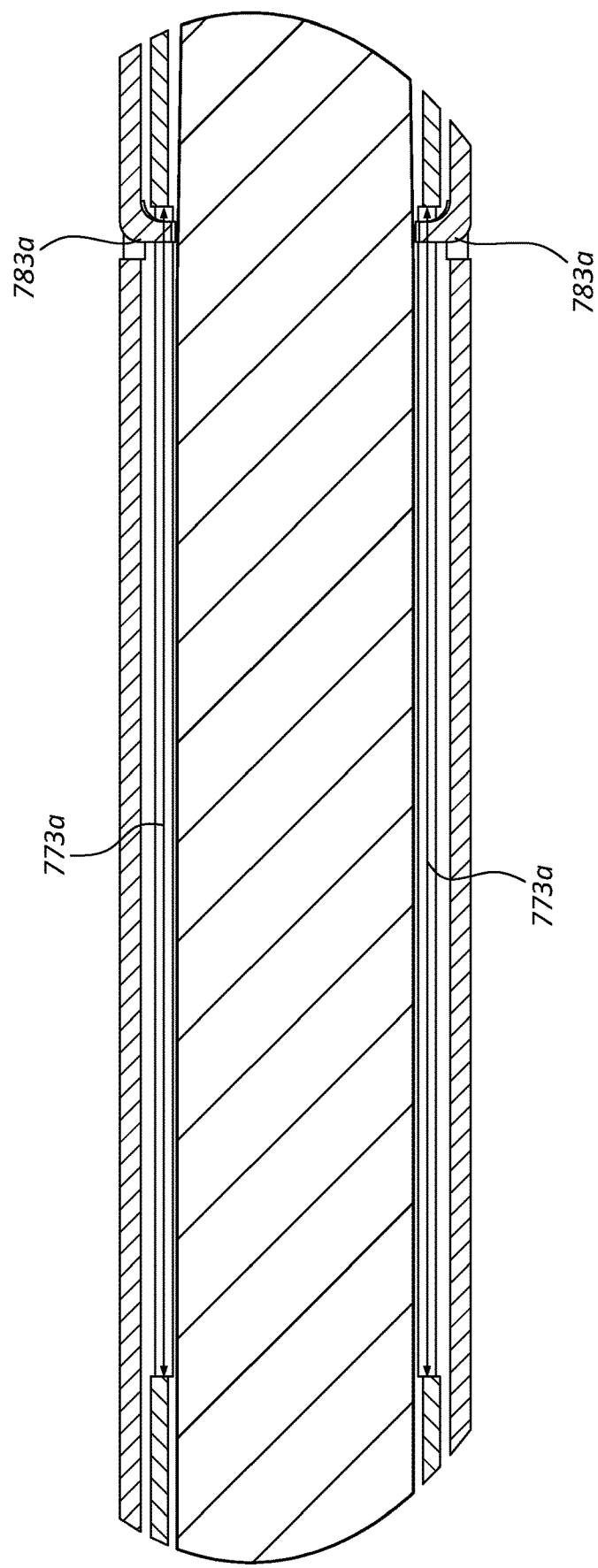
FIG. 45 is an enlarged view of a portion of the cross-sectional view of FIG. 44, taken around line 45-45.

FIG. 44 is an enlarged view of a portion of the cross-sectional view of FIG. 42, taken around line 44-44. FIG. 44 illustrates two slots 773a of the cannula 770 as well as two tabs 783a of the outer tubular member 780. The stylet 760 is also shown. FIG. 45 is a further enlarged view of a portion of the cross-sectional view of FIG. 44, taken around line 45-45, further illustrating a slots 773a and tabs 783a. In the illustrated embodiment, two slots 773a and tabs 783a, disposed at 180 degrees to each other, are shown. In some embodiments, the assemblies may comprise multiple slots and tabs positioned around a circumference of the assembly at the same longitudinal position. In some embodiments they may be equally spaced, while in other embodiments they may be irregularly spaced. Further, additional slots (such as 773b of FIG. 39) and tabs (such as 783b of FIG. 40) may be positioned at other longitudinal points on the assemblies.

Referencing FIGS. 38-45, the tabs 783a, 783b may be configured to engage the slots 773a, 773b such that the outer tubular member 780 and cannula 770 are coupled such that they cannot rotate relative to each other at the engagement point. In some assemblies, both the outer tubular member 780 and cannula 770 may be configured with flexible segments which may comprise one or more spiral cuts on each member. These flexible segments may have differing spring constants, and thus the outer tubular member 780 and cannula 770 of an assembly may tend to rotate to different degrees as the assembly is advanced along a path. Thus, the tabs 783a, 783b and slots 773a, 773b may be configured to retain the relative rotational positions of the outer tubular member 780 and cannula 770 as the assembly is advanced along a path. Retention of such alignment may tend to keep other components (such as the cutting member 785 and opening 775 of FIG. 46A) aligned while the assembly is in use. Further, the slots 773a, 773b may be sized such that the cannula 770 and outer tubular member 780 may be axially displaceable relative to each other (for example during actuation of the assembly as described below) while still retaining the rotational positions of these components. In some embodiments the tabs may be disposed on the cannula 770 and configured to interact with slots on the outer tubular member 780.

FIGS. 46A-46E are side views of a portion of the biopsy assembly of FIG. 36 in five configurations. The outer tubular member 780, cutting member 785, cannula 770, distal tip of the cannula 772, opening 775, stylet 760, and distal tip of the stylet 762 are shown in these views.

The configurations of FIGS. 46A-46E illustrate five positions of the assembly during a procedure. As with any other biopsy assembly disclosed herein, the biopsy assembly of these figures may be used in connection with a variety of procedures, including transvascular procedures. In some embodiments, for example, the biopsy assembly may be advanced through an introducer sheath (such as introducer sheath 110 of FIG. 4). The assembly may be configured such that the flexible segments of the outer tubular member 780, cannula 770, and stylet 760 are disposed within a curved portion (such as the curved distal tip 112 of FIG. 4) when the biopsy assembly is actuated to obtain a sample. Further, displacement of particular portions of the biopsy assembly may be controlled by a handle (such as handle 155 of FIG. 20). In some embodiments, springs or other mechanisms may displace the components of the biopsy assembly to obtain a sample once the biopsy assembly is actuated.

Figure 46A:
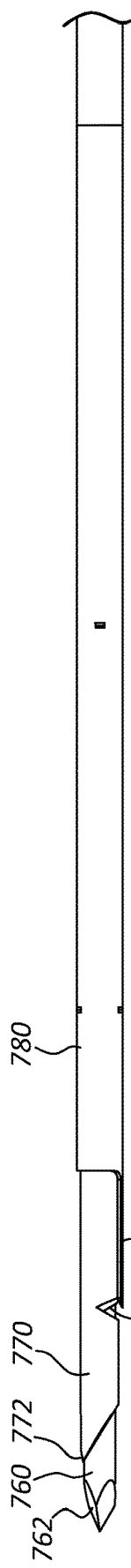
FIG. 46A is a side view of a portion of the biopsy assembly of FIG. 36 in a first configuration.

In some embodiments the biopsy assembly may be advanced within a sheath or other path with the components in the configuration shown in FIG. 46A. In this configuration, the biopsy assembly may be advanced along a delivery lumen and/or be pushed into tissue until the biopsy assembly is adjacent tissue to be biopsied. The distal tip 762 of the stylet 760 may be configured to pierce or separate tissue as the assembly is advanced within tissue. While the assembly is advanced or operated, the slots (773a of FIG. 45) and tabs (783a of FIG. 45) may resist relative rotation of the outer tubular member 780 and cannula 770 with respect to each other.

Figure 46B:
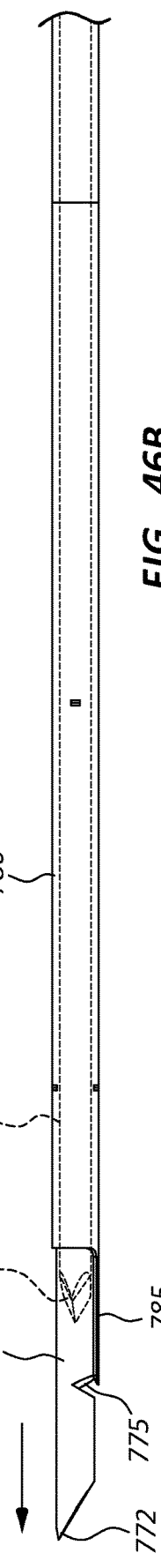
FIG. 46B is a side view of a portion of the biopsy assembly of FIG. 36 in a second configuration.
Figure 46C:
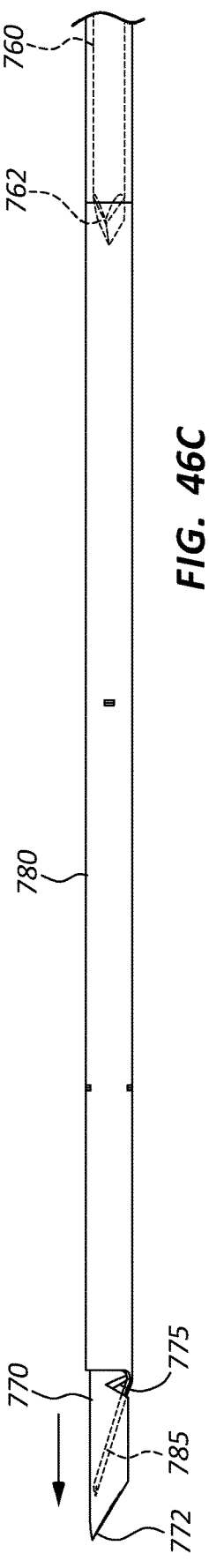
FIG. 46C is a side view of a portion of the biopsy assembly of FIG. 36 in a third configuration.
Figure 46D:
FIG. 46D is a side view of a portion of the biopsy assembly of FIG. 36 in a fourth configuration.

As shown in FIG. 46B, the cannula 770 may be advanced distally beyond the distal tip 762 of the stylet 760 when the assembly is actuated. The distal tip 772 of the cannula 770 may extend into tissue, severing a longitudinal length of the tissue sample as the cannula 770 is advanced. As shown in FIG. 46C, the outer tubular member 780 may then be advanced with respect to the cannula 770. As the outer tubular member 780 is advanced, the cutting member 785 of the outer tubular member 780 may pass through the opening 775 in the cannula 770 such that the cutting member 785 severs a distal end of the tissue sample. A tissue sample may then be disposed proximally of the cutting member 785 and distally of the distal tip 762 of the stylet 760. The entire assembly may then be retracted together, as shown in FIG. 46D, to retrieve the tissue sample from the body. For example, the assembly may be pulled back along a delivery path in the configuration of FIG. 46D with a sample disposed within the assembly, between the cutting member 785 and the distal tip 762 of the stylet 760.

Figure 46E:
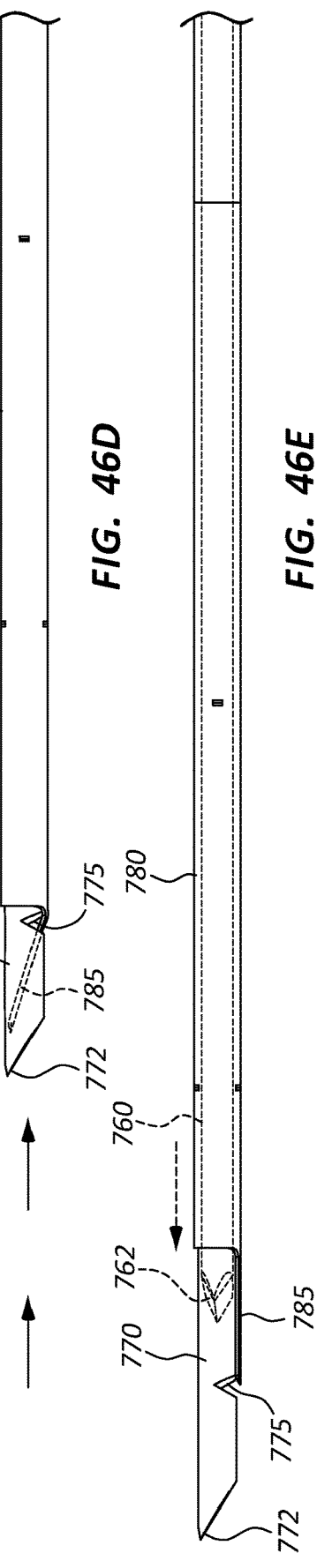
FIG. 46E is a side view of a portion of the biopsy assembly of FIG. 36 in a fifth configuration.

Once removed from the patient, the cannula 770 may be advanced with respect to the outer tubular member 780 such that the cutting member 785 is no longer disposed within the cannula 770, as shown in FIG. 46E. The stylet 760 may then be advanced with respect to the cannula 770 and outer tubular member 780 such that the stylet 760 forces the sample out of the cannula 770.

Without further elaboration, it is believed that one skilled in the art can use the preceding description to utilize the present disclosure to its fullest extent. The examples and embodiments disclosed herein are to be construed as merely illustrative and exemplary and not a limitation of the scope of the present disclosure in any way. It will be apparent to those having skill in the art, and having the benefit of this disclosure, that changes may be made to the details of the above-described embodiments without departing from the underlying principles of the disclosure herein.

The invention claimed is:

1. A transvascular liver therapy device comprising:
an elongate member comprising:
a proximal segment;
a flexible segment distal of the proximal segment, the flexible segment comprising:
a hollow member having at least one spiral cut extending between an inside diameter and an outside diameter of the hollow member; and
one or more struts disposed along the path of the spiral cut, the one or more struts configured to transfer longitudinal forces along the length of the flexible segment,
wherein at least one of the struts comprises a ball portion extending from a side of the spiral cut and a socket portion disopsed in an opposite side of the spiral cut, a portion of the ball portion disposed in a portion of the socket portion such that flex along and around the at least one of the struts is allowed,
wherein the ball portion comprises a rounded ball shape with a top portion removed such that a top of the ball portion disposed opposite the spiral cut does not contact the socket portion, and
wherein the flexible segment is more flexible that the proximal segment; and
an operative segment disposed distal of the flexible segment.

2. The transvascular liver therapy device of claim 1, wherein the flexible segment comprises a circular cross-section, the proximal segment comprises a circular cross-section, and wherein the flexible segment has a smaller outside diameter than the proximal segment.

3. The transvascular liver therapy device of claim 1, wherein the proximal segment comprises a hollow member integrally formed with the hollow member of the flexible segment.

4. The transvascular liver therapy device of claim 1, wherein the liver therapy device comprises a transjugular liver biopsy device.

5. The transvascular liver therapy device of claim 4, wherein the elongate member comprises a stylet having a circular cross-section, the operative segment comprising a partial core trough portion.

6. The transvascular liver therapy device of claim 5, further comprising a hollow cannula disposed around the stylet, the cannula comprising a proximal segment, a flexible segment distal of the proximal segment, and an operative segment disposed distal of the flexible segment.

7. The transvascular liver therapy device of claim 6, wherein the flexible segment of the elongate member and the flexible segment of the cannula are disposed adjacent each other.

8. The transvascular liver therapy device of claim 6, wherein the proximal and operative segments of the cannula comprise solid walls.

9. The transvascular liver therapy device of claim 1, wherein the spiral cut is disposed about the flexible segment at between about four and about ten revolutions per inch.

10. The transvascular liver therapy device of claim 6, wherein the proximal and operative segments of the cannula comprise solid walls and the flexible segment of the cannula comprises more than one spiral cut in a wall of the flexible segment.

11. The transvascular liver therapy device of claim 1, wherein the spiral cut has a constant pitch along the entire flexible segment.

12. The transvascular liver therapy device of claim 1, wherein the flexible segment comprises two or more struts disposed along the path of the spiral cut, and wherein at least one strut comprises a solid member, and at least one other strut comprises the ball portion and the socket portion.

13. A transjugular liver biopsy device comprising:
a cannula comprising a proximal segment; a flexible segment distal of the proximal segment of the cannula, the flexible segment being more flexible than the proximal segment of the cannula; and a cannula operative segment disposed distal of the flexible segment;
a stylet disposed within the cannula, the cannula configured to extend distally beyond the stylet to obtain a tissue sample;
an outer tubular member disposed around the cannula, comprising;
a proximal segment;
a flexible segment distal of the proximal segment of the outer tubular member, the flexible segment being more flexible than the proximal segment of the outer tubular member,
an outer tubular member operative segment disposed distal of the flexible segment comprising a cutting member coupled to an outer tubular member, the cutting member configured to server a distal end of a tissue sample when the outer tubular member is displaced distally with respect to the cannula; and an engagement feature configured to prevent rotation of the outer tubular member with respect to the cannula and the cannula with respect to the outer tubular member, wherein the engagement feature comprises:

an elongate slot disposed in a longitudinal direction and extending through a wall of the cannula from an inside diameter surface to an outside diameter surface of the wall of the cannula; and a tab coupled to the turular membeer, wherein the elongate slot is configured to engage the tab such that the elongate slot and the tab are axially displaceable relative to each other while the elongate slot are engaged.

14. The transvascular liveer therapy device of claim 1, wherein the spiral cut transitions from a shallow pitch at an end of the flexible segment and a steeper pitch at a midpoint of the flexible segment.

15. The transjugular liver biopsy device of claim 13, comprising two or more engagement features.

16. The transvascular liver therapy device of claim 1, wherein in a compressed configuration, the top of the ball portion does not contact the socket portion.

17. The transjugular liver biopsy device of claim 13, wherein the tab is slidable in the axial direction within the elongate slot.

18. The transvascular liver therapy device of claim 1, wherein the cannula operative segment comprises an opening extending through the cannula wall, and wherein the cutting member is configured to pass through the opening upon distal displacement of the outer member with respect to the cannula.

* * * * *

UNITED STATES PATENT AND TRADEMARK OFFICE
CERTIFICATE OF CORRECTION

PATENT NO. : 10,638,964 B2  
APPLICATION NO. : 14/134280  
DATED : May 5, 2020  
INVENTOR(S) : Lampropoulos et al.

Page 1 of 1

It is certified that error appears in the above-identified patent and that said Letters Patent is hereby corrected as shown below:

In the Claims

Column 19, Line 60 reads, "portion disoped..." which should read, "portion disposed..."

Column 20, Line 1 reads, "...is more flexible that..." which should read, "...is more flexible than..."

Column 20, Line 35 reads, "at between about four and about ten..." which should read, "at between four and ten..."

Column 20, Line 59 reads, "comprising;" which should read, "comprising:"

Column 20, Line 64 reads, "member, an outer..." which should read, "member; an outer..."

Column 21, Line 1 reads, "...configured to server..." which should read, "...configured to sever..."

Column 21, Line 12 reads, "...to the turular member..." which should read, "...to the tubular member..."

Column 21, Line 15-16 reads, "...while the elongate slot are engaged." which should read, "...while the elongate slot and the tab are engaged."

Column 21, Line 17 reads, "...transvascular liveer..." which should read, "...transvascular liver..."

Signed and Sealed this  
Twenty-first Day of July, 2020

Andrei Iancu  
*Director of the United States Patent and Trademark Office*